United States Patent
Liu et al.

(10) Patent No.: US 9,624,481 B2
(45) Date of Patent: Apr. 18, 2017

(54) POLYPEPTIDES HAVING BETA-XYLOSIDASE ACTIVITY AND POLYNUCLEOTIDES ENCODING SAME

(71) Applicant: Novozymes Inc., Davis, CA (US)

(72) Inventors: Ye Liu, Beijing (CN); Lan Tang, Beijing (CN); Yu Zhang, Beijing (CN); Junxin Duan, Beijing (CN)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 14/357,611

(22) PCT Filed: Nov. 30, 2012

(86) PCT No.: PCT/CN2012/085644
§ 371 (c)(1),
(2) Date: May 13, 2014

(87) PCT Pub. No.: WO2013/079015
PCT Pub. Date: Jun. 6, 2013

(65) Prior Publication Data
US 2014/0273119 A1  Sep. 18, 2014

Related U.S. Application Data

(60) Provisional application No. 61/577,917, filed on Dec. 20, 2011.

(30) Foreign Application Priority Data

Dec. 1, 2011  (WO) ................ PCT/CN2011/083276

(51) Int. Cl.
| | | |
|---|---|---|
| *A01H 5/10* | (2006.01) |
| *C12N 15/82* | (2006.01) |
| *C12N 15/55* | (2006.01) |
| *C12P 7/10* | (2006.01) |
| *C12N 9/42* | (2006.01) |
| *C12P 19/14* | (2006.01) |
| *C12P 19/02* | (2006.01) |

(52) U.S. Cl.
CPC ............ *C12N 9/2434* (2013.01); *C12P 19/02* (2013.01); *C12P 19/14* (2013.01); *C12Y 302/01037* (2013.01); *C12P 2203/00* (2013.01)

(58) Field of Classification Search
None
See application file for complete search history.

(56) References Cited

U.S. PATENT DOCUMENTS

2010/0143971 A1* 6/2010 Spodsberg ........... C12N 9/2434
435/69.1

FOREIGN PATENT DOCUMENTS

| WO | 2011038019 A1 | 3/2011 |
| WO | 2011079048 A2 | 6/2011 |

OTHER PUBLICATIONS

Barker et al. Mechanism of xylobiose hydrolysis by GH43 beta-xylosidase. 2010. J. Phys. Chem. 114(15389-15393).*
Guo et al. Protein tolerance to random amino acid change. 2004. PNAS 101(25):9205-9210.*
Uniprot. Heavy metal translocating P-type ATPase. 2006. Accession QoA7G8.*
Uniprot. Podospora anserina S mat+ genomic DNA chromosome 4, supercontig 4. 2008. Accession B2ARI1.*
Uniprot Accession B2ARI1 (first available online in 2008).*
Uniprot Accession Q0A7G8 (first available online in 2006).*
Friedberg (Brief. Bioinformatics (2006) 7: 225-242).*
Lacombe et al (Science (2001) vol. 292, pp. 1486-1487).*
Uniprot (2008. Accession B2ARI1).*
Barker et al (2010. J. Phys. Chem. 114:15389-15393).*
Uniprot (2006. Accession Q0A7G8).*
Berka et al., Genbank Accession No. AE064167 (2011).
Birren et al., Genbank Accession No. EAU38164 (2010).
Nierman et al., Genbank Accession No. XP_001265653 (2008).
Gomes et al, 1994, J Biotechnol 37(1), 11-22.
Fedorova et al, 2007—Uniport Access No. A1CYD6.
Khandke et al, 1989, Arch Biochem Biophys 274(2), 491-500.
Yu et al, 1987, Enzy Microbiol Technol 9(1), 16-24.

* cited by examiner

*Primary Examiner* — Lee A Visone
(74) *Attorney, Agent, or Firm* — Robert Starnes

(57) ABSTRACT

Provided are isolated polypeptides having beta-xylosidase activity and polynucleotides encoding the polypeptides. Also provided are nucleic acid constructs, vectors and host cells comprising the polynucleotides as well as methods of producing and using the polypeptides.

20 Claims, 3 Drawing Sheets

SEQUENCE LISTING

<160> NUMBER OF SEQ ID NOS: 12

<210> SEQ ID NO 1
<211> LENGTH: 1766
<212> TYPE: DNA
<213> ORGANISM: Thermoascus aurantiacus

<400> SEQUENCE: 1

```
atgttcctct cactatggct cgctgcattg ggacttgcct catcagccat ctcatggtct    60
ctaccgaatt ccacgtacga aaccccatt cttccaggct tccatcctga tcctagctgc   120
atctttgtgg aggagtggga cagaaccttc ttctgtgctt cgtcgagctt tctggccttc   180
cccggcattc aatccacgc aagcaaagac ctgctagatt ggaaattgat aagcaatgcg   240
ctgaaccgtc cggatcaatt gcccatgctg ccaatacca gcgggcagac aagtggcatc   300
tgggccccgt ctctcagata ctacagggg acattctacg tggtgacgac attggtccat   360
gacgacagag acgccttcga cgcgtctcgc tgggacaaca tcatcttttc aaccaaggat   420
ccgtacgacg cggcatcatg gtccgctgct gtgcattttc cgttcgaggg ctacgacacc   480
agcccgttct gggacgatga cggccaagtc tacatagcag gggctcacgc gtggaaagtt   540
cggcccggca tcgactttt cactatcgat ctcgaaacgg agaagcggg ccttcgaag   600
aatatctgga tggcacggg aggccttgcg ccagaaggac ccatatata caagaaggat   660
ggatactact acctcatgat cgccgagggc ggtacaggtc tcaaccacat ggagacagtc   720
gccagatcag aatccatcga tggcccctac gagtcgaatc ctgcgaatcc gatcctgaca   780
aacgcaaaca caacccagtt ctttcaagcc gttggccatg cggacctttt tcaagacgcc   840
atcggaaact ggtggggtgt tgcgctctcc cagaggtcag gcccagacgg tgtgacatgt   900
cccatgggcc gcgagaccgt tctatatccc gtcacctgga agcacggctc ctggcccgtg   960
acgtccagag tccaggggat catgagcgga tggcccttc cgcctcggac cagggctata  1020
cggggcaatg gtgcattcgt gtcggatcca gattacctcg attttgcacc ggggactaaa  1080
atcccttctc acttcctgca ctggcggttc ccgcgcgcag aggcctacat gatctcccct  1140
ccaggccacc cttacagtct ccgtctgaga ccgtcgaaac tgaatctgac ggcctacgat  1200
ggaagatcgg caccgggcga ccagacgttg ctggcacgtc gacaagtgga caccctgttc  1260
acgtccagcg tggacataca attctctccg cggcagcagg aggaagaagc aggcgtcact  1320
gttttcctca ctcagggaca ccatctcgac tggggcatcg tcctttttgcc cctccccaac  1380
agcacgacat tggcgccgca tttccgtttc cgcgcggaga gctacctccc ggtgcctgag  1440
ccggttgtta cggtgatccc tgatgcctgg cggaaagaga gtatcaggat ggagatcaag  1500
gccgtgaatt tcacgcacta ttcttttgct gcgggtccag cggccgatct gtcgcagatg  1560
actacgtttg catacgcgcc gggaagcctc gttacctggg gctttactgg taagtttcg  1620
gggttcggga gctcgtgtaa atactcttgc tgatgtttgc aggtgctctt gtaggtgttt  1680
acgcgacgag taatggaggg aacgggacta gtgaggctta cgtgcgcaat ggagatata  1740
tagggcaggg tcaaatcatc agctag                                       1766
```

<210> SEQ ID NO 2
<211> LENGTH: 570
<212> TYPE: PRT
<213> ORGANISM: Thermoascus aurantiacus

<400> SEQUENCE: 2

```
Met Phe Leu Ser Leu Trp Leu Ala Ala Leu Gly Leu Ala Ser Ser Ala
1               5                   10                  15

Ile Ser Trp Ser Leu Pro Asn Ser Thr Tyr Glu Asn Pro Ile Leu Pro
            20                  25                  30

Gly Phe His Pro Asp Pro Ser Cys Ile Phe Val Glu Glu Trp Asp Arg
        35                  40                  45
```

-continued

```
Thr Phe Phe Cys Ala Ser Ser Phe Leu Ala Phe Gly Ile Pro
    50                  55                  60

Ile His Ala Ser Lys Asp Leu Leu Asp Trp Lys Leu Ile Ser Asn Ala
65                  70                  75                  80

Leu Asn Arg Pro Asp Gln Leu Pro Met Leu Ala Asn Thr Ser Gly Gln
                85                  90                  95

Thr Ser Gly Ile Trp Ala Pro Ser Leu Arg Tyr Tyr Arg Gly Thr Phe
                100                 105                 110

Tyr Val Val Thr Thr Leu Val His Asp Asp Arg Asp Ala Phe Asp Ala
            115                 120                 125

Ser Arg Trp Asp Asn Ile Ile Phe Ser Thr Lys Asp Pro Tyr Asp Ala
    130                 135                 140

Ala Ser Trp Ser Ala Ala Val His Phe Pro Phe Glu Gly Tyr Asp Thr
145                 150                 155                 160

Ser Pro Phe Trp Asp Asp Gly Gln Val Tyr Ile Ala Gly Ala His
                165                 170                 175

Ala Trp Lys Val Arg Pro Gly Ile Asp Phe Phe Thr Ile Asp Leu Glu
            180                 185                 190

Thr Gly Glu Ala Gly Pro Ser Lys Asn Ile Trp Asn Gly Thr Gly Gly
    195                 200                 205

Leu Ala Pro Glu Gly Pro His Ile Tyr Lys Lys Asp Gly Tyr Tyr Tyr
210                 215                 220

Leu Met Ile Ala Glu Gly Gly Thr Gly Leu Asn His Met Glu Thr Val
225                 230                 235                 240

Ala Arg Ser Glu Ser Ile Asp Gly Pro Tyr Glu Ser Asn Pro Ala Asn
                245                 250                 255

Pro Ile Leu Thr Asn Ala Asn Thr Thr Gln Phe Phe Gln Ala Val Gly
            260                 265                 270

His Ala Asp Leu Phe Gln Asp Ala Ile Gly Asn Trp Trp Gly Val Ala
    275                 280                 285

Leu Ser Gln Arg Ser Gly Pro Asp Gly Val Thr Cys Pro Met Gly Arg
290                 295                 300

Glu Thr Val Leu Tyr Pro Val Thr Trp Lys His Gly Ser Trp Pro Val
305                 310                 315                 320

Thr Ser Arg Val Gln Gly Ile Met Ser Gly Trp Pro Leu Pro Pro Arg
                325                 330                 335

Thr Arg Ala Ile Arg Gly Asn Gly Ala Phe Val Ser Asp Pro Asp Tyr
            340                 345                 350

Leu Asp Phe Ala Pro Gly Thr Lys Ile Pro Ser His Phe Leu His Trp
    355                 360                 365

Arg Phe Pro Arg Ala Glu Ala Tyr Met Ile Ser Pro Pro Gly His Pro
370                 375                 380

Tyr Ser Leu Arg Leu Arg Pro Ser Lys Leu Asn Leu Thr Ala Tyr Asp
385                 390                 395                 400

Gly Arg Ser Ala Pro Gly Asp Gln Thr Leu Leu Ala Arg Arg Gln Val
                405                 410                 415

Asp Thr Leu Phe Thr Ser Ser Val Asp Ile Gln Phe Ser Pro Arg Gln
            420                 425                 430

Gln Glu Glu Glu Ala Gly Val Thr Val Phe Leu Thr Gln Gly His His
    435                 440                 445

Leu Asp Trp Gly Ile Val Leu Leu Pro Leu Pro Asn Ser Thr Thr Leu
450                 455                 460
```

Ala Pro His Phe Arg Phe Arg Ala Glu Ser Tyr Leu Pro Val Pro Glu
465                 470                 475                 480

Pro Val Val Thr Val Ile Pro Asp Ala Trp Arg Lys Glu Ser Ile Arg
            485                 490                 495

Met Glu Ile Lys Ala Val Asn Phe Thr His Tyr Ser Phe Ala Ala Gly
        500                 505                 510

Pro Ala Ala Asp Leu Ser Gln Met Thr Thr Phe Ala Tyr Ala Pro Gly
            515                 520                 525

Ser Leu Val Thr Trp Gly Phe Thr Gly Ala Leu Val Gly Val Tyr Ala
        530                 535                 540

Thr Ser Asn Gly Gly Asn Gly Thr Ser Glu Ala Tyr Val Arg Asn Trp
545                 550                 555                 560

Arg Tyr Ile Gly Gln Gly Gln Ile Ile Ser
                565                 570

<210> SEQ ID NO 3
<211> LENGTH: 1310
<212> TYPE: DNA
<213> ORGANISM: Thermoascus aurantiacus

<400> SEQUENCE: 3

| | | |
|---|---|---|
| atgttgctcg catttgcatt gatttctttg ctatctatat gttattcttt caaacttccg | 60 |
| ttcgagcgcc gcgacgattt tccagggccc catggcaccg gactccagat ccatgaccca | 120 |
| agcatcatca agtcggggga ttcctactat gcgtacggtg tcgaccgaa tatcagtata | 180 |
| tttcaatccc ccggtctaga tggaccttgg gaaaaggttg gaactgtgct agacgggcca | 240 |
| agtgtgatca agaaaggcga caatatcgct ccatgggcac ccactgtcat ccagcatggc | 300 |
| gacacgtttt actgctacta gtgttagc caagccgggt gtcgagacag cgccattggt | 360 |
| gtaacaacct cgaagacacc aggacatggc ggatgggtag atcatggcct catagttcag | 420 |
| tcagggaatg gcgaaggagc caatgtgcat ccctttgaca gtccaacac atcgatccg | 480 |
| catgtttttg tcacagcaga tggcaaaggc tatctgacct ttggcagttt ctggactggc | 540 |
| gtctggcagg ttcctctggc tccggacctg aaatcggtcc tgaatccaaa gcacccagat | 600 |
| gcaaagaacc tcgtctacga gccaaaaccg cttgacgctg gtggttcgga tccaaaccct | 660 |
| cttttgccgcg atgagacggg ttcacatcct gtggaagggg ccaccatgag ctaccgagac | 720 |
| ggatggtatt atctctggta cagccatgga agatgctgcg acctcaatct caacgcgctc | 780 |
| ccggcgcccg aggacctgta aggctgaatg atctcttcag catcgtctcc cataatgaca | 840 |
| tattagctga cttgtctgca acagatatag tatcagagtc ggaaggtcca ggagtcctac | 900 |
| aggtccattc gtcgatcgca atggcatcga tttggtaaag ggaggcggca ctattgctta | 960 |
| cgcttctaat ggccatgtgc ttgcaccggg agggcagggg gtattggccg atggagacac | 1020 |
| agatattcta tactaccatt accgtaagtg accacttcta ccactcctca ctacctcgga | 1080 |
| cgagataagt aactgacggt gttccaaat agtggacaag aacattggcc ttggatttg | 1140 |
| ggtctgtttg acatttccct atatccctaa aaagattttc ggcagtgatg tgcctaacgc | 1200 |
| aagcgatagg acgcccagat gggctataat cctctgaaat atgtcgacgg ctggcctgtt | 1260 |
| gccatatgag ccgacggaat agtgtaaccg tgaggtgtac cgccggaata | 1310 |

<210> SEQ ID NO 4
<211> LENGTH: 354
<212> TYPE: PRT
<213> ORGANISM: Thermoascus aurantiacus

<400> SEQUENCE: 4

```
Met Leu Leu Ala Phe Ala Leu Ile Ser Leu Ser Ile Cys Tyr Ser
1               5                   10                  15

Phe Lys Leu Pro Phe Glu Arg Arg Asp Asp Phe Pro Gly His Gly
            20                  25                  30

Thr Gly Leu Gln Ile His Asp Pro Ser Ile Ile Lys Val Gly Asp Ser
        35                  40                  45

Tyr Tyr Ala Tyr Gly Val Gly Pro Asn Ile Ser Ile Phe Gln Ser Pro
    50                  55                  60

Gly Leu Asp Gly Pro Trp Glu Lys Val Gly Thr Val Leu Asp Gly Pro
65              70                  75                  80

Ser Val Ile Lys Lys Gly Asp Asn Ile Ala Pro Trp Ala Pro Thr Val
                85                  90                  95

Ile Gln His Gly Asp Thr Phe Tyr Cys Tyr Ser Val Ser Gln Ala
                100                 105                 110

Gly Cys Arg Asp Ser Ala Ile Gly Val Thr Thr Ser Lys Thr Pro Gly
            115                 120                 125

His Gly Gly Trp Val Asp His Gly Leu Ile Val Gln Ser Gly Asn Gly
            130                 135                 140

Glu Gly Ala Asn Val His Pro Phe Asp Lys Ser Asn Thr Ile Asp Pro
145                 150                 155                 160

His Val Phe Val Thr Ala Asp Gly Lys Gly Tyr Leu Thr Phe Gly Ser
                165                 170                 175

Phe Trp Thr Gly Val Trp Gln Val Pro Leu Ala Pro Asp Leu Lys Ser
            180                 185                 190

Val Leu Asn Pro Lys His Pro Asp Ala Lys Asn Leu Val Tyr Glu Pro
            195                 200                 205

Lys Pro Leu Asp Ala Gly Ser Asp Pro Asn Pro Leu Cys Arg Asp
210                 215                 220

Glu Thr Gly Ser His Pro Val Glu Gly Ala Thr Met Ser Tyr Arg Asp
225                 230                 235                 240

Gly Trp Tyr Tyr Leu Trp Tyr Ser His Gly Arg Cys Cys Asp Leu Asn
            245                 250                 255

Leu Asn Ala Leu Pro Ala Pro Glu Asp Leu Tyr Ser Ile Arg Val Gly
            260                 265                 270

Arg Ser Arg Ser Pro Thr Gly Pro Phe Val Asp Arg Asn Gly Ile Asp
            275                 280                 285

Leu Val Lys Gly Gly Thr Ile Ala Tyr Ala Ser Asn Gly His Val
            290                 295                 300

Leu Ala Pro Gly Gly Gln Gly Val Leu Ala Asp Gly Asp Thr Asp Ile
305                 310                 315                 320

Leu Tyr Tyr His Tyr Leu Asp Lys Asn Ile Gly Leu Gly Phe Trp Asp
                325                 330                 335

Ala Gln Met Gly Tyr Asn Pro Leu Lys Tyr Val Asp Gly Trp Pro Val
            340                 345                 350

Ala Ile
```

<210> SEQ ID NO 5
<211> LENGTH: 1749
<212> TYPE: DNA
<213> ORGANISM: Thermoascus aurantiacus

<400> SEQUENCE: 5
atgaaggttc tcgcggcgct cggcctgctg gccacggccg tgagtggtgc caacttcaat    60

-continued

```
cagccggttc tttgggagga cctggcggac ctggatgtct tccgtgtggg aagcaagttc    120
tactattcgg cctcgaccat gcattactct cccggagctc cgattctcga atcttccgat    180
ctggtgaact gggactacat cggacattcg gtcccgtccc taaactgggg ctccaagtat    240
gacttgcagg gcggtcgcgc ctacgtcaag ggcatctggg cctcatctct ccggtaccgt    300
gagaagacca agacctggta ctggattgga tgtgtcgagt tcagcaagac atacatctat    360
acggcgccct cggccaccgg cccttggaag cagagcggca tgatcaacca atgctattac    420
gactgcggct tgttgatcga cgacgacgat atcatgtacg tggcctacgg aggcacggac    480
attagcgtgg cccaactgtc ctcggacggt ctcagtcagg tgaagacgca aaaggtcttc    540
tcctcgacca tcggtgccat cgaaggatcg cgcttttacc acattaatgg ggcatactac    600
atcttcaaca ccctccccgc caacgcggaa tacgttctca gtccaacag tccatggggt    660 ccttacacgc aaaaattgct ggagaagaat atcgcaactc cgatccaagg gggtggtatc    720
ccgcatcaag gaggcatcgt cgacacccca gatggaaaat ggtactacat ggccttcgtg    780
gacgcctatc cgggtggccg cgtacctgtt ctggcgccca tcacctgggg atccgatgga    840
ttcccccagg tcactaccgt gaacggaggc tggggcactt cctacccata cccaatgacc    900
ccccagatct cctcaagtcc gaccggcaca gacaccttcc gaggaacctc tttgggtccg    960
cagtgggaat ggaatcacaa ccccgacacc aactccttca cggtcaacaa cggcttgacc   1020
ttgcgcactg ccaccaagac caatgatctg tactcggcac gcaacactct cactcatcgc   1080
attctgggtc ctcagtccta cgcgaccgtt gaattgagca tcggcagcat gctctcgggg   1140
gatcgcagcg gtctagcgat gcttcgagac tcttcggcgt atgtggcagt ggtgaacaac   1200
ggcggcactt tccgggtcag catggtatcc ggtctcacca tggactccaa ctggaacact   1260
cagtcgacag gtcaggaggt ggctggcacc aatctccccg cgggcacctc gaagatttgg   1320
ttgcgggccg ccgccaacat tcaacccggc agtggtcgaa ccgcgacctt ctcgtacagc   1380
acggacggct cctcctttgt caaaatcggc aatccgttcg tgctgaacaa cgcctggcaa   1440
ttcttcatgg ctaccgcta tggcatcttc aattacgcca ccaccagcct cggcggtagc   1500
gtggtggtca actcatttga catgcagagt ggcgtcccgt ccgccactgg caagcccgtc   1560
acaaccaccg cgcgccagac acaacggcgg gtacagggc ccatcaccac caccgccggc   1620
agcggcggcg ctggaggaag ccagtccaaa tatgggcagt gtgggggcag cggctgggcg   1680
gggcctactg cgtgcgctcc aggaggaact tgctcctcgg tgaacccctg gtactcacaa   1740
tgcgtgtaa                                                            1749
```

<210> SEQ ID NO 6
<211> LENGTH: 582
<212> TYPE: PRT
<213> ORGANISM: Thermoascus aurantiacus

<400> SEQUENCE: 6

```
Met Lys Val Leu Ala Ala Leu Gly Leu Leu Ala Thr Ala Val Ser Gly
1               5                   10                  15

Ala Asn Phe Asn Gln Pro Val Leu Trp Glu Asp Leu Ala Asp Leu Asp
            20                  25                  30

Val Phe Arg Val Gly Ser Lys Phe Tyr Tyr Ser Ala Ser Thr Met His
        35                  40                  45

Tyr Ser Pro Gly Ala Pro Ile Leu Glu Ser Ser Asp Leu Val Asn Trp
    50                  55                  60
```

```
Asp Tyr Ile Gly His Ser Val Pro Ser Leu Asn Trp Gly Ser Lys Tyr
 65                  70                  75                  80

Asp Leu Gln Gly Gly Arg Ala Tyr Val Lys Gly Ile Trp Ala Ser Ser
                 85                  90                  95

Leu Arg Tyr Arg Glu Lys Thr Lys Thr Trp Tyr Trp Ile Gly Cys Val
            100                 105                 110

Glu Phe Ser Lys Thr Tyr Ile Tyr Thr Ala Pro Ser Ala Thr Gly Pro
        115                 120                 125

Trp Lys Gln Ser Gly Met Ile Asn Gln Cys Tyr Tyr Asp Cys Gly Leu
    130                 135                 140

Leu Ile Asp Asp Asp Ile Met Tyr Val Ala Tyr Gly Gly Thr Asp
145                 150                 155                 160

Ile Ser Val Ala Gln Leu Ser Ser Asp Gly Leu Ser Gln Val Lys Thr
                165                 170                 175

Gln Lys Val Phe Ser Ser Thr Ile Gly Ala Ile Glu Gly Ser Arg Phe
            180                 185                 190

Tyr His Ile Asn Gly Ala Tyr Tyr Ile Phe Asn Thr Leu Pro Ala Asn
        195                 200                 205

Ala Glu Tyr Val Leu Lys Ser Asn Ser Pro Trp Gly Pro Tyr Thr Gln
    210                 215                 220

Lys Leu Leu Glu Lys Asn Ile Ala Thr Pro Ile Gln Gly Gly Ile
225                 230                 235                 240

Pro His Gln Gly Gly Ile Val Asp Thr Pro Asp Gly Lys Trp Tyr Tyr
                245                 250                 255

Met Ala Phe Val Asp Ala Tyr Pro Gly Gly Arg Val Pro Val Leu Ala
            260                 265                 270

Pro Ile Thr Trp Gly Ser Asp Gly Phe Pro Gln Val Thr Thr Val Asn
        275                 280                 285

Gly Gly Trp Gly Thr Ser Tyr Pro Tyr Pro Met Thr Pro Gln Ile Ser
    290                 295                 300

Ser Ser Pro Thr Gly Thr Asp Thr Phe Arg Gly Thr Ser Leu Gly Pro
305                 310                 315                 320

Gln Trp Glu Trp Asn His Asn Pro Asp Thr Asn Ser Phe Thr Val Asn
                325                 330                 335

Asn Gly Leu Thr Leu Arg Thr Ala Thr Lys Thr Asn Asp Leu Tyr Ser
            340                 345                 350

Ala Arg Asn Thr Leu Thr His Arg Ile Leu Gly Pro Gln Ser Tyr Ala
        355                 360                 365

Thr Val Glu Leu Ser Ile Gly Ser Met Leu Ser Gly Asp Arg Ser Gly
    370                 375                 380

Leu Ala Met Leu Arg Asp Ser Ser Ala Tyr Val Ala Val Asn Asn
385                 390                 395                 400

Gly Gly Thr Phe Arg Val Ser Met Val Ser Gly Leu Thr Met Asp Ser
                405                 410                 415

Asn Trp Asn Thr Gln Ser Thr Gly Gln Glu Val Ala Gly Thr Asn Leu
            420                 425                 430

Pro Ala Gly Thr Ser Lys Ile Trp Leu Arg Ala Ala Asn Ile Gln
        435                 440                 445

Pro Gly Ser Gly Arg Thr Ala Thr Phe Ser Tyr Ser Thr Asp Gly Ser
    450                 455                 460

Ser Phe Val Lys Ile Gly Asn Pro Phe Val Leu Asn Asn Ala Trp Gln
465                 470                 475                 480

Phe Phe Met Gly Tyr Arg Tyr Gly Ile Phe Asn Tyr Ala Thr Thr Ser
```

```
                485                 490                 495
Leu Gly Gly Ser Val Val Asn Ser Phe Asp Met Gln Ser Gly Val
            500                 505                 510

Pro Ser Ala Thr Gly Lys Pro Val Thr Thr Ala Arg Gln Thr Thr
            515                 520                 525

Thr Ala Gly Thr Gly Pro Ile Thr Thr Thr Ala Gly Ser Gly Ala
            530                 535                 540

Gly Gly Ser Gln Ser Lys Tyr Gly Gln Cys Gly Gly Ser Gly Trp Ala
545                 550                 555                 560

Gly Pro Thr Ala Cys Ala Pro Gly Gly Thr Cys Ser Ser Val Asn Pro
                565                 570                 575

Trp Tyr Ser Gln Cys Val
            580

<210> SEQ ID NO 7
<211> LENGTH: 44
<212> TYPE: DNA
<213> ORGANISM: Artificial Sequence
<220> FEATURE:
<223> OTHER INFORMATION: Synthetic Construct

<400> SEQUENCE: 7
acacaactgg ggatccacca tgttcctctc actatggctc gctg                    44

<210> SEQ ID NO 8
<211> LENGTH: 52
<212> TYPE: DNA
<213> ORGANISM: Artificial Sequence
<220> FEATURE:
<223> OTHER INFORMATION: Synthetic Construct

<400> SEQUENCE: 8
gtcaccctct agatctccct tttatcacta ctagctgtct atccgttact ct          52

<210> SEQ ID NO 9
<211> LENGTH: 42
<212> TYPE: DNA
<213> ORGANISM: Artificial Sequence
<220> FEATURE:
<223> OTHER INFORMATION:
    GTCACCCTCTAGATCTcccttttatcactactagctgtctatccgttactct-3'

<400> SEQUENCE: 9
acacaactgg ggatccacca tgttgctcgc atttgcattg at                     42

<210> SEQ ID NO 10
<211> LENGTH: 36
<212> TYPE: DNA
<213> ORGANISM: Artificial Sequence
<220> FEATURE:
<223> OTHER INFORMATION: Synthetic Construct

<400> SEQUENCE: 10
gtcaccctct agatctcagg ccagccgtcg acatat                            36

<210> SEQ ID NO 11
<211> LENGTH: 40
<212> TYPE: DNA
<213> ORGANISM: Artificial Sequence
<220> FEATURE:
<223> OTHER INFORMATION: Synthetic Construct

<400> SEQUENCE: 11
```

```
acacaactgg ggatccacca tgaaggttct cgcggcgctc                          40
```

<210> SEQ ID NO 12
<211> LENGTH: 41
<212> TYPE: DNA
<213> ORGANISM: Artificial Sequence
<220> FEATURE:
<223> OTHER INFORMATION: Synthetic Construct

<400> SEQUENCE: 12

```
gtcaccctct agatctcctc atccaggaag agccgtgttt c                       41
```

POLYPEPTIDES HAVING BETA-XYLOSIDASE ACTIVITY AND POLYNUCLEOTIDES ENCODING SAME

CROSS-REFERENCE TO RELATED APPLICATIONS

This application is a 35 U.S.C. 371 national application of PCT/CN2012/085644 filed Nov. 30, 2012, which claims priority or the benefit under 35 U.S.C. 119 of PCT application no. PCT/CN2011/083276 filed Dec. 1, 2011 and U.S. provisional application No. 61/577,917 filed Dec. 20, 2011, the contents of which are fully incorporated herein by reference.

STATEMENT AS TO RIGHTS TO INVENTIONS MADE UNDER FEDERALLY SPONSORED RESEARCH AND DEVELOPMENT

This invention was made with Government support under Cooperative Agreement DE-FC36-08G018080 awarded by the Department of Energy. The government has certain rights in this invention.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having beta-xylosidase activity and polynucleotides encoding the polypeptides. The present invention also relates to nucleic acid constructs, vectors, and host cells comprising the polynucleotides as well as methods of producing and using the polypeptides.

Description of the Related Art

Lignocellulose, the world's largest renewable biomass resource, is composed mainly of lignin, cellulose, and hemicellulose, of which a large part of the latter is xylan. Xylanases (e.g., endo-1,4-beta-xylanase, EC 3.2.1.8) hydrolyze internal β-1,4-xylosidic linkages in xylan to produce smaller molecular weight xylose and xylo-oligomers. Xylans are polysaccharides formed from 1,4β-glycoside-linked D-xylopyranoses. Beta-xylosidases catalyze the exo-hydrolysis of short beta (1→4)-xylooligosaccharides to remove successive D-xylose residues from non-reducing termini.

Cellulose is a polymer of the glucose linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the lignocellulose is converted to fermentable sugars, e.g., glucose, the fermentable sugars can easily be fermented by yeast into ethanol.

There is a need in the art to improve cellulolytic enzyme compositions through supplementation with additional enzymes to increase efficiency and to provide cost-effective enzyme solutions for degradation of lignocellulose.

The present invention provides polypeptides having beta-xylosidase activity and polynucleotides encoding the polypeptides.

SUMMARY OF THE INVENTION

The present invention relates to isolated polypeptides having beta-xylosidase activity selected from the group consisting of:

(a) a polypeptide having at least 60% sequence identity to the mature polypeptide of SEQ ID NO: 2 or SEQ ID NO: 4; or at least 80% sequence identity to the mature polypeptide of SEQ ID NO: 6;

(b) a polypeptide encoded by a polynucleotide that hybridizes under at least medium-high stringency conditions with (i) the mature polypeptide coding sequence of SEQ ID NO: 1 or SEQ ID NO: 3, (ii) the cDNA sequence of SEQ ID NO: 1 or SEQ ID NO: 3, or (iii) the full-length complement of (i) or (ii); or under at least high stringency conditions with the mature polypeptide coding sequence of SEQ ID NO: 5 or the full-length complement thereof;

(c) a polypeptide encoded by a polynucleotide having at least 60% sequence identity to the mature polypeptide coding sequence of SEQ ID NO: 1 or SEQ ID NO: 3, or the cDNA sequences thereof; or at least 80% sequence identity to the mature polypeptide coding sequence of SEQ ID NO: 5;

(d) a variant of the mature polypeptide of SEQ ID NO: 2, SEQ ID NO: 4, or SEQ ID NO: 6 comprising a substitution, deletion, and/or insertion at one or more (e.g., several) positions; and (e) a fragment of the polypeptide of (a), (b), (c), or (d) that has beta-xylosidase activity.

The present invention also relates to isolated polynucleotides encoding the polypeptides of the present invention; nucleic acid constructs, recombinant expression vectors, and recombinant host cells comprising the polynucleotides; and methods of producing the polypeptides.

The present invention also relates to processes for degrading or converting a cellulosic or xylan-containing material, comprising: treating the cellulosic or xylan-containing material with an enzyme composition in the presence of a polypeptide having beta-xylosidase activity of the present invention. In one aspect, the processes further comprise recovering the degraded or converted cellulosic or xylan-containing material.

The present invention also relates to processes of producing a fermentation product, comprising: (a) saccharifying a cellulosic or xylan-containing material with an enzyme composition in the presence of a polypeptide having beta-xylosidase activity of the present invention; (b) fermenting the saccharified cellulosic or xylan-containing material with one or more (e.g., several) fermenting microorganisms to produce the fermentation product; and (c) recovering the fermentation product from the fermentation.

The present invention also relates to processes of fermenting a cellulosic or xylan-containing material, comprising: fermenting the cellulosic or xylan-containing material with one or more (e.g., several) fermenting microorganisms, wherein the cellulosic or xylan-containing material is saccharified with an enzyme composition in the presence of a polypeptide having beta-xylosidase activity of the present invention. In one aspect, the fermenting of the cellulosic or xylan-containing material produces a fermentation product. In another aspect, the processes further comprise recovering the fermentation product from the fermentation.

The present invention also relates to a polynucleotide encoding a signal peptide comprising or consisting of amino acids 1 to 18 of SEQ ID NO: 2, amino acids 1 to 16 of SEQ ID NO: 4, or amino acids 1 to 16 of SEQ ID NO: 6, which is operably linked to a gene encoding a protein, wherein the protein is foreign to the signal peptide; nucleic acid constructs, expression vectors, and recombinant host cells comprising the polynucleotides; and methods of producing a protein.

DEFINITIONS

Figure 1:
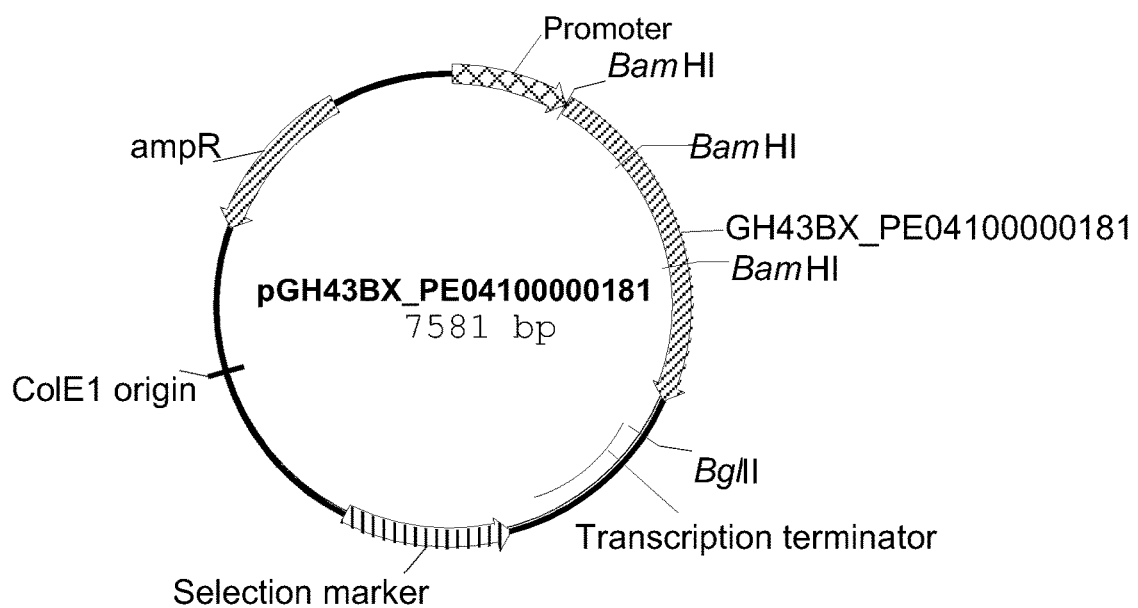
FIG. 1 shows a restriction map of plasmid pGH43BX_PE04100000181.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenylacetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 µmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 µl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 µmole of glucuronic or 4-O-methylglucuronic acid per minute at pH 5, 40° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 µmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 µmole of p-nitrophenolate anion produced per minute at 40° C., pH 5 from 1 mM p-nitrophenyl-beta-D-xyloside as substrate in 100 mM sodium citrate containing 0.01% TWEEN® 20.

The polypeptides of the present invention have at least 20%, e.g., at least 40%, at least 50%, at least 60%, at least 70%, at least 80%, at least 90%, at least 95%, and at least 100% of the beta-xylosidase activity of the mature polypeptide of SEQ ID NO: 2, SEQ ID NO: 4, or SEQ ID NO: 6.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters*, 149: 152-156; van Tilbeurgh and Claeyssens, 1985, *FEBS Letters*, 187: 283-288; and Tomme et al., 1988, *Eur. J. Biochem.* 170: 575-581.

Cellulolytic enzyme or cellulase: The term "cellulolytic enzyme" or "cellulase" means one or more (e.g., several)

enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Cellulosic Material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity may be determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids absent from the amino and/or carboxyl terminus of a mature polypeptide main; wherein the fragment has beta-xylosidase activity. In one aspect, a fragment contains at least 475 amino acid residues, e.g., at least 500 amino acid residues or at least 525 amino acid residues of SEQ ID NO: 2. In another aspect, a fragment contains at least 285 amino acid residues, e.g., at least 300 amino acid residues or at least 315 amino acid residues of SEQ ID NO: 4. In another aspect, a fragment contains at least 480 amino acid residues, e.g., at least 505 amino acid residues or at least 530 amino acid residues of SEQ ID NO: 6.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 19 to 570 of SEQ ID NO: 2 (P241QE) based on the SignalP program (Nielsen et al., 1997, Protein Engineering 10: 1-6) that predicts amino acids 1 to 18 of SEQ ID NO: 2 are a signal peptide. In another aspect, the mature polypeptide is amino acids 17 to 354 of SEQ ID NO: 4 (P241QF) based on the SignalP program that predicts amino acids 1 to 16 of SEQ ID NO: 4 are a signal peptide. In another aspect, the mature polypeptide is amino acids 17 to 582 of SEQ ID NO: 6 (P24617) based on the SignalP program that predicts amino acids 1 to 16 of SEQ ID NO: 6 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having beta-xylosidase activity. In one aspect, the mature polypeptide coding sequence is nucleotides 55 to 1763 of SEQ ID NO: 1 (D72UGP) or the cDNA sequence thereof based on the SignalP program (Nielsen et al., 1997, supra) that predicts nucleotides 1 to 54 of SEQ ID NO: 1 encode a signal peptide. In another aspect, the mature polypeptide coding sequence is nucleotides 49 to 1266 of SEQ ID NO: 3 (D72UGQ) or the cDNA sequence thereof based on the SignalP program that predicts nucleotides 1 to 48 of SEQ ID NO: 3 encode a signal peptide. In another aspect, the mature polypeptide coding sequence is nucleotides 49 to 1746 of SEQ ID NO: 5 (D827Q6) based on the SignalP program that predicts nucleotides 1 to 48 of SEQ ID NO: 5 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In a preferred aspect, a mixture of CELLUCLAST® 1.5L (Novozymes A/S, Bagsvrd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Pretreated corn stover: The term "PCS" or "Pretreated Corn Stover" means a cellulosic material derived from corn stover by treatment with heat and dilute sulfuric acid, alkaline pretreatment, or neutral pretreatment.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having beta-xylosidase activity. In one aspect, a subsequence contains at least 1425 nucleotides, e.g., at least 1500 nucleotides or at least 1575 nucleotides of SEQ ID NO: 1. In another aspect, a subsequence contains at least 855 nucleotides, e.g., at least 900 nucleotides or at least 945 nucleotides of SEQ ID NO: 3. In another aspect, a subsequence contains at least 1440 nucleotides, e.g., at least 1515 nucleotides or at least 1590 nucleotides of SEQ ID NO: 5.

Variant: The term "variant" means a polypeptide having beta-xylosidase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune*, *FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

DETAILED DESCRIPTION OF THE INVENTION

Polypeptides Having Beta-Xylosidase Activity

In an embodiment, the present invention relates to isolated polypeptides having a sequence identity to the mature polypeptide of SEQ ID NO: 2 or SEQ ID NO: 4 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; or the mature polypeptide of SEQ ID NO: 6 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; which have beta-xylosidase activity. In one aspect, the polypeptides differ by up to 10 amino acids, e.g., 1, 2, 3, 4, 5, 6, 7, 8, 9, or 10, from the mature polypeptide of SEQ ID NO: 2, SEQ ID NO: 4, or SEQ ID NO: 6.

A polypeptide of the present invention preferably comprises or consists of the amino acid sequence of SEQ ID NO: 2, SEQ ID NO: 4, or SEQ ID NO: 6; or an allelic variant thereof; or is a fragment thereof having beta-xylosidase activity. In another aspect, the polypeptide comprises or consists of the mature polypeptide of SEQ ID NO: 2, SEQ ID NO: 4, or SEQ ID NO: 6. In another aspect, the polypeptide comprises or consists of amino acids 19 to 570 of SEQ ID NO: 2, amino acids 17 to 354 of SEQ ID NO: 4, or amino acids 17 to 582 of SEQ ID NO: 6.

In another embodiment, the present invention relates to isolated polypeptides having beta-xylosidase activity encoded by polynucleotides that hybridize under very low stringency conditions, low stringency conditions, medium stringency conditions, medium-high stringency conditions, high stringency conditions, or very high stringency conditions with (i) the mature polypeptide coding sequence of SEQ ID NO: 1, SEQ ID NO: 3, or SEQ ID NO: 5, (ii) the cDNA sequence of SEQ ID NO: 1 or SEQ ID NO: 3, or (iii) the full-length complement of (i) or (ii) (Sambrook et al., 1989, *Molecular Cloning, A Laboratory Manual*, 2d edition, Cold Spring Harbor, N.Y.).

The polynucleotide of SEQ ID NO: 1, SEQ ID NO: 3, or SEQ ID NO: 5, or a subsequence thereof, as well as the polypeptide of SEQ ID NO: 2, SEQ ID NO: 4, or SEQ ID NO: 6, the mature polypeptide thereof, or a fragment thereof, may be used to design nucleic acid probes to identify and clone DNA encoding polypeptides having beta-xylosidase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having beta-xylosidase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, SEQ ID NO: 3, or SEQ ID NO: 5, the mature polypeptide coding sequences thereof, or subsequences thereof, the carrier material is used in a Southern blot.

For purposes of the present invention, hybridization indicates that the polynucleotide hybridizes to a labeled nucleic acid probe corresponding to (i) SEQ ID NO: 1, SEQ ID NO: 3, or SEQ ID NO: 5; (ii) the mature polypeptide coding sequence of SEQ ID NO: 1, SEQ ID NO: 3, or SEQ ID NO: 5; (iii) the cDNA sequence of SEQ ID NO: 1 or SEQ ID NO: 3; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is a polynucleotide that encodes the polypeptide of SEQ ID NO: 2, SEQ ID NO: 4, or SEQ ID NO: 6; the mature polypeptide thereof; or a fragment thereof. In another aspect, the nucleic acid probe is SEQ ID NO: 1, SEQ ID NO: 3, or SEQ ID NO: 5; the mature polypeptide coding sequences thereof; or the cDNA sequence of SEQ ID NO: 1 or SEQ ID NO: 3, or the mature polypeptide coding sequences thereof.

In another embodiment, the present invention relates to isolated polypeptides having beta-xylosidase activity encoded by polynucleotides having a sequence identity to the mature polypeptide coding sequence of SEQ ID NO: 1 or SEQ ID NO: 3 or the cDNA sequences thereof of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; or the mature polypeptide coding sequence of SEQ ID NO: 5 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2, SEQ ID NO: 4, or SEQ ID NO: 6 comprising a substitution, deletion, and/or insertion at one or more (e.g., several) positions. In an embodiment, the number of amino acid substitutions, deletions and/or insertions introduced into the mature polypeptide of SEQ ID NO: 2, SEQ ID NO: 4, or SEQ ID NO: 6 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine).

Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for beta-xylosidase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48.

Sources of Polypeptides Having Beta-Xylosidase Activity

A polypeptide having beta-xylosidase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In one aspect, the polypeptide is a *Thermoascus* polypeptide. In another aspect, the polypeptide is a *Thermoascus aurantiacus* polypeptide. In another aspect, the polypeptide is a *Penicillium* polypeptide. In another aspect, the polypeptide is a *Penicillium oxalicum* polypeptide. It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding a polypeptide of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Thermoascus* or *Penicillium*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, SEQ ID NO: 3, or SEQ ID NO: 5, or the cDNA sequence of the mature polypeptide coding sequence of SEQ ID NO: 1 or SEQ ID NO: 3, by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more (e.g., several) control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more (e.g., several) convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (e.g., several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more (e.g., several) control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se.

Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally (b) recovering the polypeptide. In one aspect, the cell is of the genus *Penicillium*. In another aspect, the cell is a *Penicillium oxalicum* cell. In another aspect, the cell is of the genus *Thermoascus*. In another aspect, the cell is a *Thermoascus aurantiacus* cell.

The present invention also relates to methods of producing a polypeptide of the present invention, comprising (a) cultivating a recombinant host cell of the present invention under conditions conducive for production of the polypeptide; and optionally (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a whole fermentation broth comprising a polypeptide of the present invention is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide may be constructed in accordance with methods known in the art. In short, the plant or plant cell is constructed by incorporating one or more expression constructs encoding the polypeptide into the plant host genome or chloroplast genome and propagating the resulting modified plant or plant cell into a transgenic plant or plant cell.

The expression construct is conveniently a nucleic acid construct that comprises a polynucleotide encoding a polypeptide operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide in the plant. For instance, the promoter enhancer element may be an intron that is placed between the promoter and the polynucleotide encoding a polypeptide. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention comprising (a) cultivating a transgenic plant or a plant cell comprising a polynucleotide encoding the polypeptide under conditions conducive for production of the polypeptide; and optionally (b) recovering the polypeptide.

Removal or Reduction of Beta-Xylosidase Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of the polynucleotide using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may be accomplished by insertion, substitution, or deletion of one or more nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

The present invention also relates to methods of inhibiting the expression of a polypeptide having beta-xylosidase activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (sRNA) or a micro RNA (miRNA). In a preferred aspect, the dsRNA is small interfering RNA for inhibiting transcription. In another preferred aspect, the dsRNA is micro RNA for inhibiting translation.

The present invention also relates to such double-stranded RNA (dsRNA) molecules, comprising a portion of the mature polypeptide coding sequence of SEQ ID NO: 1, SEQ ID NO: 3, or SEQ ID NO: 5 for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

The present invention further relates to a mutant cell of a parent cell that comprises a disruption or deletion of a polynucleotide encoding the polypeptide or a control sequence thereof or a silenced gene encoding the polypeptide, which results in the mutant cell producing less of the polypeptide or no polypeptide compared to the parent cell.

The polypeptide-deficient mutant cells are particularly useful as host cells for expression of native and heterologous polypeptides. Therefore, the present invention further relates to methods of producing a native or heterologous polypeptide, comprising (a) cultivating the mutant cell under conditions conducive for production of the polypeptide; and optionally (b) recovering the polypeptide. The term "heterologous polypeptides" means polypeptides that are not native to the host cell, e.g., a variant of a native protein. The host cell may comprise more than one copy of a polynucleotide encoding the native or heterologous polypeptide.

The methods used for cultivation and purification of the product of interest may be performed by methods known in the art.

The methods of the present invention for producing an essentially beta-xylosidase-free product is of particular interest in the production of eukaryotic polypeptides, in particular fungal proteins such as enzymes. The beta-xylosidase-deficient cells may also be used to express heterologous proteins of pharmaceutical interest such as hormones, growth factors, receptors, and the like. The term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from beta-xylosidase activity that is produced by a method of the present invention.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing. In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The fermentation broth formulations or cell compositions may further comprise multiple enzymatic activities, such as one or more (e.g., several) enzymes selected from the group consisting of a cellulase, a hemicellulase, an esterase, an expansin, a laccase, a ligninolytic enzyme, a pectinase, a peroxidase, a protease, and a swollenin. The fermentation broth formulations or cell compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The cell-killed whole broth or composition may contain the unfractionated contents of the fermentation materials derived at the end of the fermentation. Typically, the cell-killed whole broth or composition contains the spent cell culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of preferred uses of the compositions of the present invention. The dosage of the composition and other conditions under which the composition is used may be determined on the basis of methods known in the art.

Enzyme Compositions

The present invention also relates to compositions comprising a polypeptide of the present invention. Preferably, the compositions are enriched in such a polypeptide. The term "enriched" indicates that the beta-xylosidase activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of a cellulase, a hemicellulase, an esterase, an expansin, a laccase, a ligninolytic enzyme, a pectinase, a peroxidase, a protease, and a swollenin. The compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase. The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Uses

The present invention is also directed to the following processes for using the polypeptides having beta-xylosidase activity, or compositions thereof.

The present invention also relates to processes for degrading or converting a cellulosic or xylan-containing material, comprising: treating the cellulosic or xylan-containing material with an enzyme composition in the presence of a polypeptide having beta-xylosidase activity of the present invention. In one aspect, the processes further comprise recovering the degraded or converted cellulosic or xylan-containing material. Soluble products of degradation or conversion of the cellulosic or xylan-containing material can be separated from insoluble cellulosic or xylan-containing material using a method known in the art such as, for example, centrifugation, filtration, or gravity settling.

The present invention also relates to processes of producing a fermentation product, comprising: (a) saccharifying a cellulosic or xylan-containing material with an enzyme composition in the presence of a polypeptide having beta-xylosidase activity of the present invention; (b) fermenting the saccharified cellulosic or xylan-containing material with one or more (e.g., several) fermenting microorganisms to produce the fermentation product; and (c) recovering the fermentation product from the fermentation.

The present invention also relates to processes of fermenting a cellulosic or xylan-containing material, comprising: fermenting the cellulosic or xylan-containing material with one or more (e.g., several) fermenting microorganisms, wherein the cellulosic or xylan-containing material is saccharified with an enzyme composition in the presence of a polypeptide having beta-xylosidase activity of the present invention. In one aspect, the fermenting of the cellulosic or xylan-containing material produces a fermentation product. In another aspect, the processes further comprise recovering the fermentation product from the fermentation.

The processes of the present invention can be used to saccharify the cellulosic or xylan-containing material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic or xylan-containing material typically involves pretreatment, enzymatic hydrolysis (saccharification), and fermentation.

The processing of the cellulosic or xylan-containing material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include fluidized bed, upflow blanket, immobilized, and extruder type reactors for hydrolysis and/or fermentation.

Pretreatment. In practicing the processes of the present invention, any pretreatment process known in the art can be used to disrupt plant cell wall components of the cellulosic or xylan-containing material (Chandra et al., 2007, Substrate pretreatment: The key to effective enzymatic hydrolysis of lignocellulosics?, *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic or xylan-containing material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic or xylan-containing material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic or xylan-containing material is heated to disrupt the plant cell wall components, including lignin, hemicellulose, and cellulose to make the cellulose and other fractions, e.g., hemicellulose, accessible to enzymes. The cellulosic or xylan-containing material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic or xylan-containing material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic or xylan-containing material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous countercurrent shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic or xylan-containing material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic or xylan-containing material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. and Biotechnol. Vol.* 105-108, p. 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic or xylan-containing material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic or xylan-containing material is present during pretreatment in amounts preferably between 10-80 wt ° A), e.g., 20-70 wt ° A) or 30-60 wt ° A), such as around 40 wt %. The pretreated cellulosic or xylan-containing material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic or xylan-containing material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic or xylan-containing material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic or xylan-containing material. Biological pretreatment techniques can involve applying lignin-solubilizing microorganisms and/or enzymes (see, for example, Hsu, T.-A., 1996, *Pretreatment of biomass*, in *Handbook on Bioethanol: Production and Utilization*, Wyman, C. E., ed., Taylor & Francis, Washington, D.C., 179-212; Ghosh and Singh, 1993, *Physicochemical and biological treatments for enzymatic/microbial conversion of cellulosic biomass, Adv. Appl. Microbiol.* 39: 295-333; McMillan, J. D., 1994, *Pretreating lignocellulosic biomass: a review*, in Enzymatic Conversion of Biomass for Fuels Production, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification In the hydrolysis step, also known as saccharification, the cellulosic or xylan-containing material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition as described herein in the presence of a polypeptide having beta-xylosidase activity of the present invention. The enzyme components of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme components, i.e., optimal for the enzyme components. The hydrolysis can be carried out as a fed batch or continuous process where the cellulosic or xylan-containing material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

The enzyme compositions can comprise any protein useful in degrading or converting the cellulosic or xylan-containing material.

In one aspect, the enzyme composition comprises or further comprises one or more (e.g., several) proteins selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endoglucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin In the processes of the present invention, the enzyme(s) can be added prior to or during saccharification, saccharification and fermentation, or fermentation.

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and polypeptides having beta-xylosidase activity depend on several factors including, but not limited to, the mixture of cellulolytic and/or hemicellulolytic enzyme components, the cellulosic or xylan-containing material, the concentration of cellulosic or xylan-containing material, the pretreatment(s) of the cellulosic or xylan-containing material, temperature, time, pH, and inclusion of fermenting organism (e.g., yeast for Simultaneous Saccharification and Fermentation).

In one aspect, an effective amount of cellulolytic or hemicellulolytic enzyme to the cellulosic or xylan-containing material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic or xylan-containing material.

In another aspect, an effective amount of a polypeptide having beta-xylosidase activity to the cellulosic or xylan-containing material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic or xylan-containing material.

In another aspect, an effective amount of a polypeptide having beta-xylosidase activity to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic or xylan-containing material, e.g., GH61 polypeptides having cellulolytic enhancing activity (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a Gram-positive bacterial polypeptide such as a *Bacillus, Streptococcus, Streptomyces, Staphylococcus, Enterococcus, Lactobacillus, Lactococcus, Clostridium, Geobacillus, Caldicellulosiruptor, Acidothermus, Thermobifidia,* or *Oceanobacillus* polypeptide having enzyme activity, or a Gram negative bacterial polypeptide such as an *E. coli, Pseudomonas, Salmonella, Campylobacter, Helicobacter, Flavobacterium, Fusobacterium, Ilyobacter, Neisseria,* or *Ureaplasma* polypeptide having enzyme activity.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having enzyme activity.

In another aspect, the polypeptide is a *Streptococcus equisimilis, Streptococcus pyogenes, Streptococcus uberis,* or *Streptococcus equi* subsp. *Zooepidemicus* polypeptide having enzyme activity.

In another aspect, the polypeptide is a *Streptomyces achromogenes, Streptomyces avermitilis, Streptomyces coelicolor, Streptomyces griseus,* or *Streptomyces lividans* polypeptide having enzyme activity.

The polypeptide having enzyme activity may also be a fungal polypeptide, and more preferably a yeast polypeptide such as a *Candida, Kluyveromyces, Pichia, Saccharomyces, Schizosaccharomyces,* or *Yarrowia* polypeptide having enzyme activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having enzyme activity.

In one aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having enzyme activity.

In another aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride,* or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), FILTRASE® NL (DSM); METHAPLUS® S/L 100 (DSM), ROHAMENT™ 7069 W (Rohm GmbH), FIBREZYME® LDI (Dyadic International, Inc.), FIBREZYME® LBR (Dyadic International, Inc.), or VISCOSTAR® 150L (Dyadic International, Inc.). The cellulase enzymes are added in amounts effective from about 0.001 to about 5.0 wt % of solids, e.g., about 0.025 to about 4.0 wt % of solids or about 0.005 to about 2.0 wt % of solids.

Examples of bacterial endoglucanases that can be used in the processes of the present invention, include, but are not limited to, an Acidothermus *cellulolyticus* endoglucanase (WO 91/05039; WO 93/15186; U.S. Pat. No. 5,275,944; WO 96/02551; U.S. Pat. No. 5,536,655, WO 00/70031, WO 05/093050); Thermobifida *fusca* endoglucanase III (WO 05/093050); and Thermobifida *fusca* endoglucanase V (WO 05/093050).

Examples of fungal endoglucanases that can be used in the present invention, include, but are not limited to, a *Trichoderma reesei* endoglucanase I (Penttila et al., 1986, *Gene* 45: 253-263, *Trichoderma reesei* Cel7B endoglucanase I (GENBANK™ accession no. M15665), *Trichoderma reesei* endoglucanase II (Saloheimo, et al., 1988, *Gene* 63:11-22), *Trichoderma reesei* Cel5A endoglucanase II (GENBANK™ accession no. M19373), *Trichoderma reesei* endoglucanase III (Okada et al., 1988, *Appl. Environ. Micro-*

*biol.* 64: 555-563, GENBANK™ accession no. AB003694), *Trichoderma reesei* endoglucanase V (Saloheimo et al., 1994, *Molecular Microbiology* 13: 219-228, GENBANK™ accession no. Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Erwinia* carotovara endoglucanase (Saarilahti et al., 1990, *Gene* 90: 9-14), *Fusarium oxysporum* endoglucanase (GENBANK™ accession no. L29381), *Humicola grisea* var. *thermoidea* endoglucanase (GENBANK™ accession no. AB003107), *Melanocarpus albomyces* endoglucanase (GENBANK™ accession no. MAL515703), *Neurospora crassa* endoglucanase (GENBANK™ accession no. XM_324477), *Humicola insolens* endoglucanase V, *Myceliophthora thermophila* CBS 117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris* NRRL 8126 CEL7C endoglucanase, *Thielavia terrestris* NRRL 8126 CEL7E endoglucanase, *Thielavia terrestris* NRRL 8126 CEL7F endoglucanase, Cladorrhinum foecundissimum ATCC 62373 CEL7A endoglucanase, and *Trichoderma reesei* strain No. VTT-D-80133 endoglucanase (GENBANK™ accession no. M15665).

Examples of cellobiohydrolases useful in the present invention include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 2002/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637).

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027304, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 5,457,046, 5,648,263, and 5,686,593.

In the processes of the present invention, any GH61 polypeptide having cellulolytic enhancing activity can be used as a component of the enzyme composition.

Examples of GH61 polypeptides having cellulolytic enhancing activity useful in the processes of the present invention include, but are not limited to, GH61 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290), *Myceliophthora thermophila* (WO 2009/085935, WO 2009/085859, WO 2009/085864, WO 2009/085868), *Aspergillus fumigatus* (WO 2010/138754), GH61 polypeptides from *Penicillium pinophilum* (WO 2011/005867), *Thermoascus* sp. (WO 2011/039319), *Penicillium* sp. (WO 2011/041397), and *Thermoascus crustaceous* (WO 2011/041504).

In one aspect, the GH61 polypeptide having cellulolytic enhancing activity is used in the presence of a soluble activating divalent metal cation according to WO 2008/151043, e.g., manganese or copper.

In another aspect, the GH61 polypeptide having cellulolytic enhancing activity is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1, 2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of the bicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothieno-pyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl)furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of the nitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L (Biocatalysts Limit, Wales, UK), and DEPOL™ 762P (Biocatalysts Limit, Wales, UK).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thielavia terrestris* NRRL 8126 (WO 2009/079210), and *Trichophaea saccata* GH 10 (WO 2011/057083).

Examples of beta-xylosidases useful in the processes of the present invention include, but are not limited to, beta-xylosidases from *Neurospora crassa* (SwissProt accession number Q7SOW4), *Trichoderma reesei* (UniProtKB/TrEMBL accession number Q92458), and *Talaromyces emersonii* (SwissProt accession number Q8X212).

Examples of acetylxylan esterases useful in the processes of the present invention include, but are not limited to, acetylxylan esterases from *Aspergillus aculeatus* (WO 2010/108918), *Chaetomium globosum* (Uniprot accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt accession number q7s259), *Phaeosphaeria nodorum* (Uniprot accession number QOUHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt Accession number A1D9T4), *Neurospora crassa* (UniProt accession number Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt accession number alccl2), *Aspergillus fumigatus* (SwissProt accession number Q4VVVV45), *Aspergillus niger* (Uniprot accession number Q96WX9), *Aspergillus terreus* (SwissProt accession number QOCJP9), *Humicola insolens* (WO 2010/014706), *Penicillium aurantiogriseum* (WO 2009/068565), *Talaromyces emersonii* (UniProt accession number Q8X211), and *Trichoderma reesei* (Uniprot accession number Q99024).

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation. The fermentable sugars obtained from the hydrolyzed cellulosic or xylan-containing material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic or xylan-containing material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic or xylan-containing material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is (are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida*, *Kluyveromyces*, and *Saccharomyces*, e.g., *Candida sonorensis*, *Kluyveromyces marxianus*, and *Saccharomyces cerevisiae*.

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans*; *Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis*, and *C. scehatae*; *Clostridium*, such as *C. acetobutylicum, C. thermocellum*, and *C. phytofermentans*; *E. coli*, especially *E. coli* strains that have been genetically modified to improve the yield of ethanol; *Geobacillus* sp.; *Hansenula*, such as *Hansenula anomala*; *Klebsiella*, such as *K. oxytoca*; *Kluyveromyces*, such as *K. marxianus*, *K. lactis*, *K. thermotolerans*, and *K. fragilis*; *Schizosaccharomyces*, such as *S. pombe*; *Thermoanaerobacter*, such as *Thermoanaerobacter saccharolyticum*; and *Zymomonas*, such as *Zymomonas mobilis*.

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida blankii*. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida schehatae*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Saccharomyces* spp. In a more preferred aspect, the yeast is *Saccharomyces cerevisiae*. In another preferred aspect, the yeast is *Saccharomyces distaticus*. In another more preferred aspect, the yeast is *Saccharomyces uvarum*.

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacillus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis*, *Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic or xylan-containing material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic or xylan-containing material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products: A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy, Vol.* 13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery. The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic or xylan-containing material and purified by conventional methods of distillation. Ethanol with a purity of up to about 96 vol.% can be obtained, which can be used as, for example, fuel ethanol, drinking ethanol, i.e., potable neutral spirits, or industrial ethanol.

Signal Peptides

The present invention also relates to an isolated polynucleotide encoding a signal peptide comprising or consisting of amino acids 1 to 18 of SEQ ID NO: 2, amino acids 1 to 16 of SEQ ID NO: 4, or amino acids 1 to 16 of SEQ ID NO: 6. The polynucleotide may further comprise a gene encoding a protein, which is operably linked to the signal peptide. The protein is preferably foreign to the signal peptide. In one aspect, the polynucleotide encoding the signal peptide is nucleotides 1 to 54 of SEQ ID NO: 1. In another aspect, the polynucleotide encoding the signal peptide is nucleotides 1 to 48 of SEQ ID NO: 3. In another aspect, the polynucleotide encoding the signal peptide is nucleotides 1 to 48 of SEQ ID NO: 5.

The present invention also relates to nucleic acid constructs, expression vectors and recombinant host cells comprising such polynucleotides.

The present invention also relates to methods of producing a protein, comprising (a) cultivating a recombinant host cell comprising such a polynucleotide operably linked to a gene encoding the protein; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The gene may be obtained from any prokaryotic, eukaryotic, or other source.

The present invention is further described by the following examples that should not be construed as limiting the scope of the invention.

EXAMPLES

Strains

A fungal strain designated NN044936 was isolated from a soil sample collected from Yunnan Province, China, by dilution on PDA plates at 45° C. and then purified by transferring a single conidium onto a YG agar plate. The NN044936 strain was identified as *Thermoascus aurantiacus*, based on both morphological characteristics and ITS rDNA sequence.

A fungal strain designated NN051380 was isolated from a soil sample collected from China, by dilution on PDA plates at 25° C. and then purified by transferring a single conidium onto a PDA plate. The NN051380 strain was identified as *Penicillium oxalicum*, based on both morphological characteristics and ITS rDNA sequence.

Media

PDA plates were composed of 39 grams of potato dextrose agar and deionized water to 1 liter.

YG agar plates were composed of 5 g of yeast extract, 10 g of glucose, 20 g of agar, and deionized water to 1 liter.

YPG medium was composed of 0.4% yeast extract, 0.1% $KH_2PO_4$, 0.05% $MgSO_4.7H_2O$, and 1.5% glucose in deionized water.

YPM medium was composed of 1% of yeast extract, 2% of peptone, and 2% of maltose in deionized water.

Czapek's medium was composed of 30 g of sucrose, 3 g of $NaNO_3$, 0.5 g of $MgSO_4.7H_2O$, 0.01 g of $FeSO_4.7H_2O$, 1 g of $K_2HPO_4$, 0.5 g of KCl, and deionized water to 1 liter. The pH was adjusted to pH 4 with 1 M HCl.

Minimal medium plates were composed of 342 g of sucrose, 20 ml of salt solution, 20 g of agar, and deionized water to 1 liter. The salt solution was composed of 2.6% KCl, 2.6% $MgSO_4.7H2O$, 7.6% $KH_2PO_4$, 2 ppm $Na_2B_4O_7.10H_2O$, 20 ppm $CuSO_4.5H_2O$, 40 ppm $FeSO_4.7H_2O$, 40 ppm $MnSO_4.2H_2O$, 40 ppm $Na_2MoO_4.2H_2O$, and 400 ppm $ZnSO_4.7H_2O$ in deionized water.

Example 1

Genomic DNA Extraction

*Thermoascus aurantiacus* strain NN044936 was inoculated onto a PDA plate and incubated for 3 days at 45° C. in the darkness. Several mycelia-PDA plate plugs were inoculated into 500 ml shake flasks containing 100 ml of YPG medium. The flasks were incubated for 3 days at 45° C. with shaking at 160 rpm. The mycelia were collected by filtration through MIRACLOTH® (Calbiochem, La Jolla, Calif., USA) and frozen in liquid nitrogen. Frozen mycelia were ground, by a mortar and a pestle, to a fine powder, and genomic DNA was isolated using a DNEASY® Plant Maxi Kit (QIAGEN GmbH, Hilden, Germany) following the manufacturer's instructions.

*Penicillium oxalicum* strain NN051380 was inoculated onto a PDA plate and incubated for 5 days at 25° C. in the darkness. Several mycelia-PDA plate plugs were inoculated into 500 ml shake flasks containing 100 ml of Czapek's medium. The flasks were incubated for 3 days at 30° C. with shaking at 160 rpm. The mycelia were collected by filtration through MIRACLOTH® and frozen in liquid nitrogen. Frozen mycelia were ground, by a mortar and a pestle, to a fine powder, and the genomic DNA was isolated using a DNEASY® Plant Maxi Kit following the manufacturer's instructions.

Example 2

Genome Sequencing, Assembly and Annotation of *Thermoascus aurantiacus* NN044936 and *Penicillium oxalicum* Strain NN051380

The extracted genomic DNA samples were delivered to Beijing Genome Institute (BGI, Shenzhen, China) for genome sequencing using an ILLUMINA® GA2 System (Illumina, Inc., San Diego, Calif., USA). The raw reads were assembled at BGI using program SOAPdenovo (Li et al., 2010, *Genome Research* 20(2): 265-72). The assembled sequences were analyzed using standard bioinformatics methods for gene finding and functional prediction. GeneID (Parra et al., 2000, *Genome Research* 10(4): 511-515) was used for gene prediction. Blastall version 2.2.10 (Altschul et al., 1990, *J. Mol. Biol.* 215 (3): 403-410, National Center for Biotechnology Information (NCBI), Bethesda, Md., USA) and HMMER version 2.1.1 (National Center for Biotechnology Information (NCBI), Bethesda, Md., USA) were used to predict function based on structural homology. The beta-xylosidases were identified directly by analysis of the Blast results. The Agene program (Munch and Krogh, 2006, *BMC Bioinformatics* 7: 263) and SignalP program (Nielsen et al., 1997, *Protein Engineering* 10: 1-6) were used to identify start codons. The SignalP program was further used to predict signal peptides. Pepstats (Rice et al., 2000, *Trends Genet.* 16(6): 276-277) was used to predict the isoelectric points and molecular weights of the deduced amino acid sequences.

Example 3

Cloning of *Thermoascus aurantiacus* GH43 Beta-Xylosidase Coding Sequences from Genomic DNA Based on the DNA information (SEQ ID NOs: 1 and 3) obtained from genome sequencing in Example 2, the oligonucleotide primers shown below were designed to amplify GH43 beta-xylosidase genes, PE04100000181 and PE04100000621, from the genomic DNA of *Thermoascus aurantiacus* NN044936. Primers were synthesized by Invitrogen, Beijing, China.

SEQ ID 1_forward primer:

(SEQ ID NO: 7)
5'-ACACAACTGGGGATCCACCatgttcctctcactatggctcgctg-3'

SEQ ID 1_reverse primer:

(SEQ ID NO: 8)
GTCACCCTCTAGATCTccctttatcactactagctgtctatccgttac
tct-3'

SEQ ID 3_forward primer:

(SEQ ID NO: 9)
5'-ACACAACTGGGGATCCACCatgttgctcgcatttgcattgat-3'

SEQ ID 3_reverse primer:

(SEQ ID NO: 10)
5'-GTCACCCTCTAGATCTcaggccagccgtcgacatat-3'

Lowercase characters represent the coding regions of the genes in the forward primers and the flanking region of the gene in the reverse primers, while capitalized characters represent regions homologous to the insertion sites of plasmid pPFJO355 (WO 2011/005867).

For the GH43 beta-xylosidase genes, PE04100000181 and PE04100000621, 20 picomoles of each forward and reverse primer pair above were used in a PCR reaction composed of 2 μl of *Thermoascus aurantiacus* NN044936 genomic DNA, 10 μl of 5×GC Buffer (Finnzymes Oy, Espoo, Finland), 1.5 μl of DMSO, 2.5 mM each of dATP, dTTP, dGTP, and dCTP, and 0.6 unit of PHUSION™ High-Fidelity DNA Polymerase (Finnzymes Oy, Espoo, Finland) in a final volume of 50 μl. The amplifications were performed using a Peltier Thermal Cycler (MJ Research Inc., South San Francisco, Calif., USA) programmed for denaturing at 98° C. for 1 minute; 8 cycles of denaturing at 98° C. for 15 seconds, annealing at 65° C. for 30 seconds, with a 1° C. decrease per cycle, and elongation at 72° C. for 3.25 minutes; 22 cycles each at 98° C. for 15 seconds, 58° C. for 30 seconds, and 72° C. for 3.25 minutes; and a final extension at 72° C. for 10 minutes. The heat block then went to a 4° C. soak cycle.

The PCR products were isolated by 1.0% agarose gel electrophoresis using 90 mM Tris-borate and 1 mM EDTA (TBE) buffer where product bands of 1.7 kb and 1.2 kb for the GH43 beta-xylosidase genes, PE04100000181 and PE04100000621, respectively, were visualized under UV light. The PCR products were then excised from the gel and purified using an ILLUSTRA® GFX® PCR DNA and Gel Band Purification Kit (GE Healthcare, Buckinghamshire, UK) according to the manufacturer's instructions.

Plasmid pPFJO355 was digested with Bam HI and Bgl II, isolated by 1.0% agarose gel electrophoresis using TBE buffer, and purified using an ILLUSTRA® GFX® PCR DNA and Gel Band Purification Kit according to the manufacturer's instructions.

TABLE 1

Figure 2:
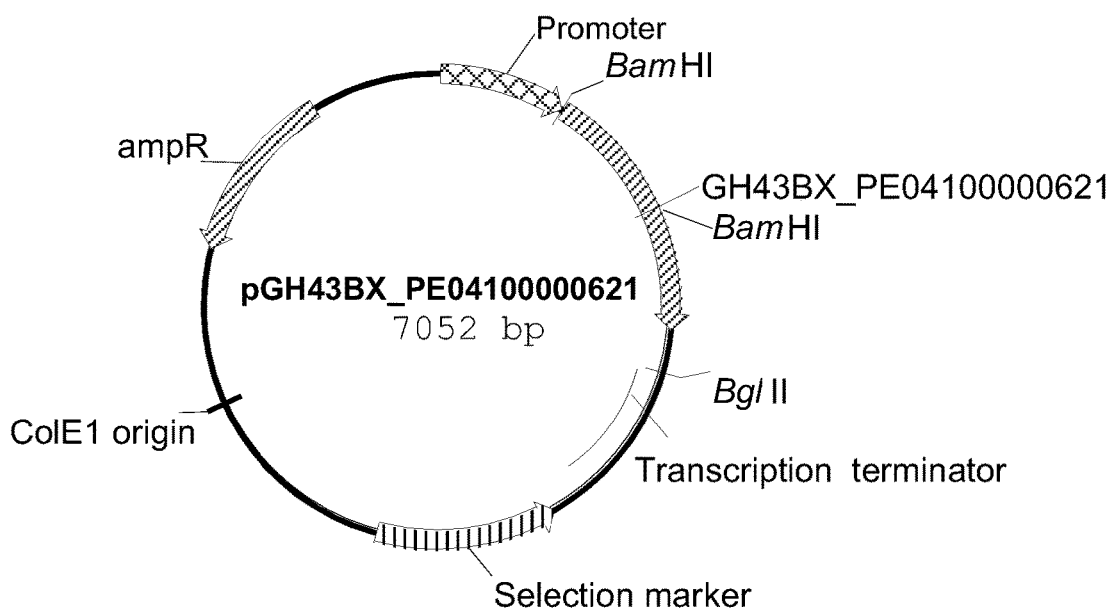
FIG. 2 shows a restriction map of plasmid pGH43BX_PE04100000621.

| Plasmids | | |
| --- | --- | --- |
| Gene name | Plasmid | DNA map |
| PE04100000181 | pGH43BX_PE04100000181 | FIG. 1 |
| PE04100000621 | pGH43BX_PE04100000621 | FIG. 2 |

Each PCR product and the digested vector were ligated together using an IN-FUSION® CF Dry-down Cloning Kit (Clontech Laboratories, Inc., Mountain View, Calif., USA) resulting in the plasmids shown in Table 1: pGH43BX_PE04100000181 (FIG. 1) and pGH43BX_PE04100000621 (FIG. 2), in which transcription of the *Thermoascus aurantiacus* GH43 beta-xylosidase coding sequences was under control of an *Aspergillus oryzae* alpha-amylase gene promoter. In brief, 30 ng of pPFJO355, digested with Bam HI and Bgl II, and 60 ng of each purified *Thermoascus aurantiacus* GH43 beta-xylosidase PCR product were added to reaction vials and resuspended in a final volume of 10 μl by addition of deionized water. The reactions were incubated at 37° C. for 15 minutes and then 50° C. for 15 minutes. Three μl of the reactions were used to transform *E. coli* TOP10 competent cells (TIANGEN Biotech (Beijing) Co. Ltd., Beijing, China). *E. coli* transformants containing expression constructs were detected by colony PCR. Colony PCR is a method for quick screening of plasmid inserts directly from *E. coli* colonies. Briefly, in a premixed PCR solution aliquot in each PCR tube, including PCR buffer, MgCl$_2$, dNTPs, and primer pairs from which the PCR fragment was generated, a single colony was added by picking with a sterile tip and twirling the tip in the reaction solution. Normally 7-10 colonies were screened. After the PCR, reactions were analyzed by 1.0% agarose gel electrophoresis using TBE buffer. Plasmid DNA was prepared from colonies showing inserts with the expected sizes using a QIAprep Spin Miniprep Kit (QIAGEN Inc., Valencia, Calif., USA). The *Thermoascus aurantiacus* GH43 beta-xylosidase coding sequences inserted in pGH43BX_PE04100000181 and pGH43BX_PE04100000621 were confirmed by DNA sequencing using a 3730XL DNA Analyzer (Applied Biosystems Inc, Foster City, Calif., USA).

Example 4

Expression of *Thermoascus aurantiacus* GH43 Beta-Xylosidase Coding Sequences in *Aspergillus oryzae*

*Aspergillus oryzae* HowB101 (WO 95/035385) protoplasts prepared according to the method of Christensen et al., 1988, Bio/Technology 6: 1419-1422, were transformed with 3 μg of pGH43BX_PE04100000181 or pGH43BX_PE04100000621. Each transformation yielded about 50 transformants. Four transformants from each transformation were isolated to individual Minimal medium plates.

The four transformants from each transformation were inoculated separately into 3 ml of YPM medium in a 24-well plate and incubated at 30° C. with agitation at 150 rpm. After 3 days incubation, 20 μl of supernatant from each culture were analyzed by SDS-PAGE using a NUPAGE® NOVEX® 4-12% Bis-Tris Gel with 50 mM 2-(N-morpholino)ethanesulfonic acid (MES) (Invitrogen Corporation, Carlsbad, Calif., USA) according to the manufacturer's instructions. The resulting gel was stained with INSTANT-BLUE® (Expedeon Ltd., Babraham Cambridge, UK). SDS-PAGE profiles of the cultures showed transformants of pGH43BX_PE04100000181 and pGH43BX_PE04100000621 had a major protein band at 90 kDa and 43 kDa, respectively (Table 2). One transformant from each transformation was selected as expression strains and designated *Aspergillus oryzae* O7MRH and *Aspergillus oryzae* O7MRG, respectively.

TABLE 2

| Plasmid | Expression | |
|---|---|---|
| | Expression strain | Size of recombinant protein (kDa) |
| pGH43BX_PE04100000181 | O7MRH | 90 |
| pGH43BX_PE04100000621 | O7MRG | 43 |

Example 5

Cloning of *Penicillium oxalicum* GH43 Xylosidase Coding Sequences from Genomic DNA Based on the gene information (SEQ ID NOs: 7 and 9) obtained by genome sequencing in Example 2, the oligonucleotide primers shown below were designed to amplify a GH43 xylosidase gene, GH43_ZY569164_13, from the genomic DNA of *Penicillium oxalicum*. Primers were synthesized by Invitrogen, Beijing, China.

SEQ ID 7 forward primer:
(SEQ ID NO: 11)
5'-ACACAACTGGGGATCCACCatgaaggttctcgcggcgctc-3'

SEQ ID 7 Reverse primer:
(SEQ ID NO: 12)
5'-GTCACCCTCTAGATCTcctcatccaggaagagccgtgtttc-3'

Lowercase characters represent the DNA sequence of the gene in the forward primer and the flanking region of the gene in the reverse primer, while capitalized characters represent regions homologous to the insertion sites of plasmid pPFJO355.

For the GH43 beta-xylosidase gene, 20 picomoles of each of the primer pairs above were used in a PCR reaction composed of 3.3 μl of *Penicillium oxalicum* genomic DNA, 10 μl of 5×GC Buffer, 2.5 mM each of dATP, dTTP, dGTP, and dCTP, and 1.0 unit of PHUSION™ High-Fidelity DNA Polymerase in a final volume of 50 μl. The amplifications were performed using a Peltier Thermal Cycler programmed for denaturing at 98° C. for 2 minutes; 20 cycles each at 98° C. for 15 seconds, 55° C. for 30 seconds, and 72° C. for 105 seconds; and a final extension at 72° C. for 3 minutes. The heat block then went to a 4° C. soak cycle.

The reaction product was isolated by 1.0% agarose gel electrophoresis using TBE buffer where a product band of 1.8 kb for the GH43 beta-xylosidase gene, GH43_ZY569164_13, was visualized under UV light. The PCR product was then purified from solution using an ILLUSTRA® GFX® PCR DNA and Gel Band Purification Kit according to the manufacturer's instructions.

Plasmid pPFJO355 was digested with Bam HI and Bgl II, isolated by 1.0% agarose gel electrophoresis using TBE buffer, and purified using an ILLUSTRA® GFX® PCR DNA and Gel Band Purification Kit according to the manufacturer's instructions.

An IN-FUSION® CF Dry-down Cloning Kit was used to clone the PCR fragment directly into the expression vector pPFJO355, without the need for restriction digestion and ligation.

TABLE 3

Figure 3:
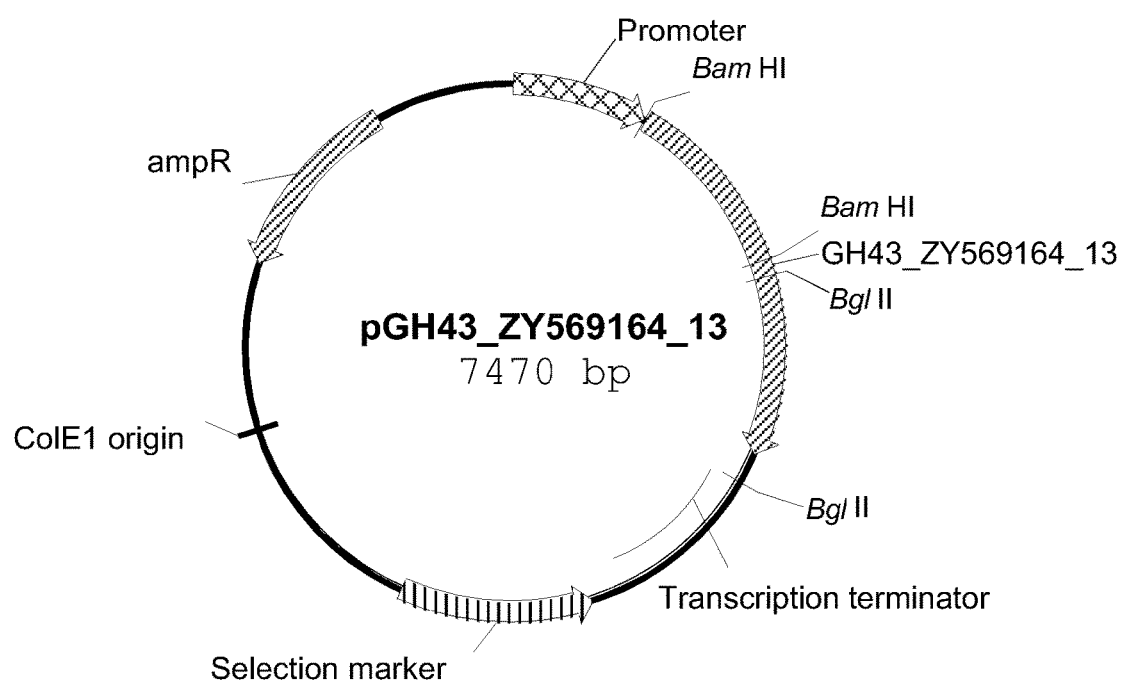
FIG. 3 shows a restriction map of plasmid pGH43_ZY569164_13.

| Gene name | Plasmid | DNA map |
|---|---|---|
| GH43_ZY569164_13 | pGH43_ZY569164_13 | FIG. 3 |

The PCR product and the digested vector were ligated together using an IN-FUSION® CF Dry-down Cloning Kit resulting in the plasmid shown in Table 3: pGH43_ZY569164_13 (FIG. 3) in which transcription of the *Penicillium oxalicum* GH43 beta-xylosidase coding sequence was under control of an *Aspergillus oryzae* alpha-amylase gene promoter. In brief, 30 ng of pPFJO355, digested with Bam HI and Bgl II, and 60 ng of the purified *Penicillium oxalicum* GH43 beta-xylosidase PCR product were added to a reaction vial and resuspended in a final volume of 10 μl by addition of deionized water. The reaction was incubated at 37° C. for 15 minutes and then 50° C. for 15 minutes. Three μl of the reaction were used to transform *E. coli* TOP10 competent cells. *E. coli* transformants containing expression constructs were detected by colony PCR as described in Example 3. Plasmid DNA was prepared using a QIAprep Spin Miniprep Kit. The *Penicillium oxalicum* GH43 beta-xylosidase coding sequence inserted in pGH43_ZY569164_13 was confirmed by DNA sequencing using a 3730XL DNA Analyzer.

Example 6

Expression of a *Penicillium oxalicum* GH43 Beta-Xylosidase Coding Sequence in *Aspergillus oryzae*

*Aspergillus oryzae* HowB101 (WO 95/035385) protoplasts prepared according to the method of Christensen et al., 1988, supra, were transformed with 3 μg of pGH43_ZY569164_13. The transformation yielded about 50 transformants. Eight transformants were isolated to individual Minimal medium plates.

Four transformants were inoculated separately into 3 ml of YPM medium in a 24-well plate and incubated at 30° C. with agitation at 150 rpm. After 3 days incubation, 20 μl of supernatant from each culture were analyzed by SDS-PAGE using a NUPAGE® NOVEX® 4-12% Bis-Tris Gel with 50 mM MES. The resulting gel was stained with INSTANT-BLUE®. The SDS-PAGE profiles of the cultures showed that the majority of the transformants had a band at approximately 63 kDa. One transformant was selected as an expression strain and designated *Aspergillus oryzae* 05SQ3.

Example 7

Characterization of the Genomic DNAs Encoding GH43 Beta-Xylosidases

The genomic DNA sequence and deduced amino acid sequence of a *Thermoascus aurantiacus* GH43 beta-xylosidase coding sequence are shown in SEQ ID NO: 1 (D72UGP) and SEQ ID NO: 2 (P241QE), respectively. The coding sequence is 1766 bp including the stop codon, which is interrupted by one intron of 53 bp (nucleotides 1610 to 1662). The encoded predicted protein is 570 amino acids. Using the SignalP program (Nielsen et al., 1997, *Protein Engineering* 10: 1-6), a signal peptide of 18 residues was predicted. The predicted mature protein contains 552 amino acids with a predicted molecular mass of 61.17 kDa and a predicted isoelectric point of 5.57.

A comparative pairwise global alignment of amino acid sequences was determined using the Needleman and Wunsch algorithm (Needleman and Wunsch, 1970, *J. Mol. Biol.* 48: 443-453) with gap open penalty of 10, gap extension penalty of 0.5, and the EBLOSUM62 matrix. The alignment showed that the deduced amino acid sequence of the *Thermoascus aurantiacus* genomic DNA encoding a GH43 beta-xylosidase shares 53.3% sequence identity (excluding gaps) to the deduced amino acid sequence of a GH43 protein from *Aspergillus fumigatus* (GENESEQP AZJ58729).

The genomic DNA sequence and deduced amino acid sequence of a *Thermoascus aurantiacus* GH43 beta-xylosidase coding sequence are shown in SEQ ID NO: 3 (D72UGQ) and SEQ ID NO: 4 (P241QF), respectively. The coding sequence is 1269 bp including the stop codon, which is interrupted by three introns of 67 bp (nucleotides 798 to 864), 69 bp (nucleotides 1044 to 1112), and 68 bp (nucleotides 1142 to 1209). The encoded predicted protein is 354 amino acids. Using the SignalP program (Nielsen et al., 1997, supra), a signal peptide of 16 residues was predicted. The predicted mature protein contains 338 amino acids with a predicted molecular mass of 36.54 kDa and a predicted isoelectric point of 5.45.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Thermoascus aurantiacus* genomic DNA encoding a GH43 beta-xylosidase shares 59.64% identity (excluding gaps) to the deduced amino acid sequence of a protein from *Aspergillus clavatus* (UNIPROT A1C7E0).

The genomic DNA sequence and deduced amino acid sequence of a *Penicillium oxalicum* GH43 beta-xylosidase coding sequence are shown in SEQ ID NO: 5 (D827Q6) and SEQ ID NO: 6 (P24617), respectively. The coding sequence is 1749 bp including the stop codon, without any introns. The encoded predicted protein is 582 amino acids. Using the SignalP program (Nielsen et al., 1997, supra), a signal peptide of 16 residues was predicted. The predicted mature protein contains 566 amino acids with a predicted molecular mass of 60.74 kDa and a predicted isoelectric point of 7.12.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Penicillium oxalicum* genomic DNA encoding a GH43 beta-xylosidase shares 79.28% identity (excluding gaps) to the deduced amino acid sequence of a beta-xylosidase from *Talaromyces stipitatus* (UNIPROT B8MPA2).

The present invention is further described by the following numbered paragraphs:

[1] An isolated polypeptide having beta-xylosidase activity, selected from the group consisting of: (a) a polypeptide having at least 60% sequence identity to the mature polypeptide of SEQ ID NO: 2 or SEQ ID NO: 4; or at least 80% sequence identity to the mature polypeptide of SEQ ID NO: 6; (b) a polypeptide encoded by a polynucleotide that hybridizes under at least medium-high stringency conditions with (i) the mature polypeptide coding sequence of SEQ ID NO: 1 or SEQ ID NO: 3, (ii) the cDNA sequence of SEQ ID NO: 1 or SEQ ID NO: 3, or (iii) the full-length complement of (i) or (ii); or under at least high stringency conditions with the mature polypeptide coding sequence of SEQ ID NO: 5 or the full-length complement thereof; (c) a polypeptide encoded by a polynucleotide having at least 60% sequence identity to the mature polypeptide of SEQ ID NO: 1 or SEQ ID NO: 3, or the cDNA sequences thereof; or at least 80% sequence identity to the mature polypeptide of SEQ ID NO: 5; (d) a variant of the mature polypeptide of SEQ ID NO: 2, SEQ ID NO: 4, or SEQ ID NO: 6 comprising a substitution, deletion, and/or insertion at one or more (e.g., several) positions; and (e) a fragment of the polypeptide of (a), (b), (c), or (d) that has beta-xylosidase activity.

[2] The polypeptide of paragraph 1, having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2 or SEQ ID NO: 4; or at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 6.

[3] The polypeptide of paragraph 1, which is encoded by a polynucleotide that hybridizes under medium-high, high, or very high stringency conditions with (i) the mature polypeptide coding sequence of SEQ ID NO: 1 or SEQ ID NO: 3, (ii) the cDNA sequence of SEQ ID NO: 1 or SEQ ID NO: 3, or (iii) the full-length complement of (i) or (ii); or under high or very high stringency conditions with the mature polypeptide coding sequence of SEQ ID NO: 5 or the full-length complement thereof.

[4] The polypeptide of paragraph 1, which is encoded by a polynucleotide having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 1 or SEQ ID NO: 3, or the cDNA sequences thereof; or at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 5.

[5] The polypeptide of paragraph 1, comprising or consisting of SEQ ID NO: 2, SEQ ID NO: 4, or SEQ ID NO: 6 or the mature polypeptide of SEQ ID NO: 2, SEQ ID NO: 4, or SEQ ID NO: 6.

[6] The polypeptide of paragraph 5, wherein the mature polypeptide is amino acids 19 to 570 of SEQ ID NO: 2, amino acids 17 to 354 of SEQ ID NO: 4, or amino acids 17 to 582 of SEQ ID NO: 6.

[7] The polypeptide of paragraph 1, which is a variant of the mature polypeptide of SEQ ID NO: 2, SEQ ID NO: 4, or SEQ ID NO: 6 comprising a substitution, deletion, and/or insertion at one or more (e.g., several) positions.

[8] The polypeptide of any of paragraphs 1-7, which is a fragment of SEQ ID NO: 2, SEQ ID NO: 4, or SEQ ID NO: 6, wherein the fragment has beta-xylosidase activity.

[9] A composition comprising the polypeptide of any of paragraphs 1-8.

[10] An isolated polynucleotide encoding the polypeptide of any of paragraphs 1-8.

[11] A nucleic acid construct or expression vector comprising the polynucleotide of paragraph 10 operably linked to one or more control sequences that direct the production of the polypeptide in an expression host.

[12] A recombinant host cell comprising the polynucleotide of paragraph 10 operably linked to one or more control sequences that direct the production of the polypeptide.

[13] A method of producing the polypeptide of any of paragraphs 1-8, comprising: cultivating a cell, which in its wild-type form produces the polypeptide, under conditions conducive for production of the polypeptide.

[14] The method of paragraph 13, further comprising recovering the polypeptide.

[15] A method of producing a polypeptide having xylanase activity, comprising: cultivating the host cell of paragraph 12 under conditions conducive for production of the polypeptide.

[16] The method of paragraph 15, further comprising recovering the polypeptide.

[17] A transgenic plant, plant part or plant cell transformed with a polynucleotide encoding the polypeptide of any of paragraphs 1-8.

[18] A method of producing a polypeptide having xylanase activity, comprising: cultivating the transgenic plant or plant cell of paragraph 17 under conditions conducive for production of the polypeptide.

[19] The method of paragraph 18, further comprising recovering the polypeptide

[20] A method of producing a mutant of a parent cell, comprising inactivating a polynucleotide encoding the polypeptide of any of paragraphs 1-8, which results in the mutant producing less of the polypeptide than the parent cell.

[21] A mutant cell produced by the method of paragraph 20.

[22] The mutant cell of paragraph 21, further comprising a gene encoding a native or heterologous protein.

[23] A method of producing a protein, comprising: cultivating the mutant cell of paragraph 21 or 22 under conditions conducive for production of the protein.

[24] The method of paragraph 23, further comprising recovering the protein.

[25] A double-stranded inhibitory RNA (dsRNA) molecule comprising a subsequence of the polynucleotide of paragraph 10, wherein optionally the dsRNA is a siRNA or a miRNA molecule.

[26] The double-stranded inhibitory RNA (dsRNA) molecule of paragraph 25, which is about 15, 16, 17, 18, 19, 20, 21, 22, 23, 24, 25 or more duplex nucleotides in length.

[27] A method of inhibiting the expression of a polypeptide having xylanase activity in a cell, comprising administering to the cell or expressing in the cell the double-stranded inhibitory RNA (dsRNA) molecule of paragraph 25 or 26.

[28] A cell produced by the method of paragraph 27.

[29] The cell of paragraph 28, further comprising a gene encoding a native or heterologous protein.

[30] A method of producing a protein, comprising: cultivating the cell of paragraph 28 or 29 under conditions conducive for production of the protein.

[31] The method of paragraph 30, further comprising recovering the polypeptide

[32] An isolated polynucleotide encoding a signal peptide comprising or consisting of amino acids 1 to 18 of SEQ ID NO: 2, amino acids 1 to 16 of SEQ ID NO: 4, or amino acids 1 to 16 of SEQ ID NO: 6.

[33] A nucleic acid construct or expression vector comprising a gene encoding a protein operably linked to the polynucleotide of paragraph 32, wherein the gene is foreign to the polynucleotide encoding the signal peptide.

[34] A recombinant host cell comprising a gene encoding a protein operably linked to the polynucleotide of paragraph 32, wherein the gene is foreign to the polynucleotide encoding the signal peptide.

[35] A method of producing a protein, comprising: cultivating a recombinant host cell comprising a gene encoding a protein operably linked to the polynucleotide of paragraph 32, wherein the gene is foreign to the polynucleotide encoding the signal peptide, under conditions conducive for production of the protein.

[36] The method of paragraph 35, further comprising recovering the protein.

[37] A process for degrading a cellulosic or xylan-containing material, comprising: treating the cellulosic or xylan-containing material with an enzyme composition in the presence of the polypeptide having xylanase activity of any of paragraphs 1-8.

[38] The process of paragraph 37, wherein the cellulosic or xylan-containing material is pretreated.

[39] The process of paragraph 37 or 38, wherein the enzyme composition comprises one or more (e.g., several) enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[40] The process of paragraph 39, wherein the cellulase is one or more enzymes selected from the group consisting of an endoglucanase, a cellobiohydrolase, and a beta-glucosidase.

[41] The process of paragraph 39, wherein the hemicellulase is one or more enzymes selected from the group consisting of a xylanase, an acetylxylan esterase, a feruloyl esterase, an arabinofuranosidase, a xylosidase, and a glucuronidase.

[42] The process of any of paragraphs 37-41, further comprising recovering the degraded cellulosic or xylan-containing material.

[43] The process of paragraph 42, wherein the degraded cellulosic or xylan-containing material is a sugar.

[44] The process of paragraph 43, wherein the sugar is selected from the group consisting of glucose, xylose, mannose, galactose, and arabinose.

[45] A process for producing a fermentation product, comprising: (a) saccharifying a cellulosic or xylan-containing material with an enzyme composition in the presence of the polypeptide having xylanase activity of any of paragraphs 1-8; (b) fermenting the saccharified cellulosic or xylan-containing material with one or more fermenting microorganisms to produce the fermentation product; and (c) recovering the fermentation product from the fermentation.

[46] The process of paragraph 45, wherein the cellulosic or xylan-containing material is pretreated.

[47] The process of paragraph 45 or 46, wherein the enzyme composition comprises one or more (e.g., several) enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[48] The process of paragraph 47, wherein the cellulase is one or more enzymes selected from the group consisting of an endoglucanase, a cellobiohydrolase, and a beta-glucosidase.

[49] The process of paragraph 47, wherein the hemicellulase is one or more enzymes selected from the group consisting of a xylanase, an acetylxylan esterase, a feruloyl esterase, an arabinofuranosidase, a xylosidase, and a glucuronidase.

[50] The process of any of paragraphs 45-49, wherein steps (a) and (b) are performed simultaneously in a simultaneous saccharification and fermentation.

[51] The process of any of paragraphs 45-50, wherein the fermentation product is an alcohol, an alkane, a cycloalkane, an alkene, an amino acid, a gas, isoprene, a ketone, an organic acid, or polyketide.

[52] A process of fermenting a cellulosic or xylan-containing material, comprising: fermenting the cellulosic or xylan-containing material with one or more (e.g., several) fermenting microorganisms, wherein the cellulosic or xylan-containing material is saccharified with an enzyme composition in the presence of the polypeptide having xylanase activity of any of paragraphs 1-8.

[53] The process of paragraph 52, wherein the fermenting of the cellulosic or xylan-containing material produces a fermentation product.

[54] The process of paragraph 53, further comprising recovering the fermentation product from the fermentation.

[55] The process of paragraph 53 or 54, wherein the fermentation product is an alcohol, an alkane, a cycloalkane, an alkene, an amino acid, a gas, isoprene, a ketone, an organic acid, or polyketide.

[56] The process of any of paragraphs 52-55, wherein the cellulosic or xylan-containing material is pretreated before saccharification.

[57] The process of any of paragraphs 52-56, wherein the enzyme composition comprises one or more (e.g., several) enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[58] The process of paragraph 57, wherein the cellulase is one or more enzymes selected from the group consisting of an endoglucanase, a cellobiohydrolase, and a beta-glucosidase.

[59] The process of paragraph 57, wherein the hemicellulase is one or more enzymes selected from the group consisting of a xylanase, an acetylxylan esterase, a feruloyl esterase, an arabinofuranosidase, a xylosidase, and a glucuronidase.

[60] A whole broth formulation or cell culture composition comprising the polypeptide of any of paragraphs 1-8.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A process for degrading or converting a cellulosic or xylan-containing material, the process comprising: treating the cellulosic or xylan-containing material with an enzyme composition and a polypeptide having beta-xylosidase activity, and recovering the degraded or converted cellulosic material; wherein the polypeptide having beta-xylosidase activity is selected from the group consisting of:
    (a) a polypeptide having at least 95% sequence identity to amino acids 19 to 570 of SEQ ID NO: 2;
    (b) a polypeptide encoded by a polynucleotide that hybridizes under very high stringency conditions with the full-length complement of nucleotides 55 to 1763 of SEQ ID NO: 1 or the cDNA of nucleotides 55 to 1763 SEQ ID NO: 1, wherein very high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 70° C.; and
    (c) a polypeptide encoded by a polynucleotide having at least 99% sequence identity to nucleotides 55 to 1763 of SEQ ID NO: 1, or the cDNA of nucleotides 55 to 1763 of SEQ ID NO: 1.

2. A process for producing a fermentation product, the process comprising:
    (a) saccharifying a cellulosic or xylan-containing material with an enzyme composition and a polypeptide having beta-xylosidase activity, wherein the polypeptide having beta-xylosidase activity is selected from the group consisting of: (1) a polypeptide having at least 95% sequence identity to amino acids 19 to 570 of SEQ ID NO: 2; (2) a polypeptide encoded by a polynucleotide that hybridizes under very high stringency conditions with the full-length complement of nucleotides 55 to 1763 of SEQ ID NO: 1 or the cDNA of nucleotides 55 to 1763 SEQ ID NO: 1, wherein very high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 70° C.; and (3) a polypeptide encoded by a polynucleotide having at least 99% sequence identity to nucleotides 55 to 1763 of SEQ ID NO: 1, or the cDNA of nucleotides 55 to 1763 of SEQ ID NO: 1;
    (b) fermenting the saccharified cellulosic or xylan-containing material with one or more fermenting microorganisms to produce the fermentation product; and
    (c) recovering the fermentation product from the fermentation.

3. A process of fermenting a cellulosic or xylan-containing material, the process comprising: fermenting the cellulosic or xylan-containing material with one or more fermenting microorganisms, wherein the cellulosic or xylan-containing material is saccharified with an enzyme composition in the presence of a polypeptide having beta-xylosidase activity, wherein the polypeptide having beta-xylosidase activity is selected from the group consisting of:
    (a) a polypeptide having at least 95% sequence identity to amino acids 19 to 570 of SEQ ID NO: 2; (b) a polypeptide encoded by a polynucleotide that hybridizes under very high stringency conditions with the full-length complement of nucleotides 55 to 1763 of SEQ ID NO: 1 or the cDNA of nucleotides 55 to 1763 SEQ ID NO: 1, wherein very high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 70° C.; and (c) a polypeptide encoded by a polynucleotide having at least 99% sequence identity to nucleotides 55 to 1763 of SEQ ID NO: 1, or the cDNA of nucleotides 55 to 1763 of SEQ ID NO: 1; and wherein the fermenting of the cellulosic material produces a fermentation product, and recovering the fermentation product from the fermentation.

4. A nucleic acid construct comprising a polynucleotide encoding a polypeptide having beta-xylosidase activity, wherein the polynucleotide is operably linked to one or more heterologous control sequences that direct the production of the polypeptide and wherein the polypeptide having beta-xylosidase activity is selected from the group consisting of: (a) a polypeptide having at least 95% sequence identity to amino acids 19 to 570 of SEQ ID NO: 2; (b) a polypeptide encoded by a polynucleotide that hybridizes under very high stringency conditions with the full-length complement of nucleotides 55 to 1763 of SEQ ID NO: 1 or the cDNA of nucleotides 55 to 1763 SEQ ID NO: 1, wherein very high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 70° C.; and (c) a polypeptide encoded by a polynucleotide having at least 99% sequence identity to nucleotides 55 to 1763 of SEQ ID NO: 1, or the cDNA of nucleotides 55 to 1763 of SEQ ID NO:1.

5. An isolated recombinant host cell comprising the nucleic acid construct of claim 4.

6. A method of producing a polypeptide having beta-xylosidase activity, the method comprising:

(a) cultivating the recombinant host cell of claim 5 under conditions conducive for production of the polypeptide; and optionally (b) recovering the polypeptide.

7. A transgenic plant, plant part or plant cell transformed with the nucleic acid construct of claim 4.

8. A method of producing a polypeptide having beta-xylosidase activity, the method comprising:

(a) cultivating the transgenic plant or plant cell of claim 7 under conditions conducive for production of the polypeptide; and optionally (b) recovering the polypeptide.

9. An isolated polynucleotide comprising a gene encoding a protein and a nucleic acid encoding a signal peptide comprising amino acids 1 to 18 of SEQ ID NO: 2, wherein said gene is foreign to and operably linked to the nucleic acid encoding the signal peptide.

10. An isolated recombinant host cell comprising the polynucleotide of claim 9.

11. A method of producing a protein, the method comprising:

(a) cultivating a recombinant host cell comprising a gene encoding a protein operably linked to the polynucleotide of claim 9, wherein the gene is foreign to the polynucleotide encoding the signal peptide, under conditions conducive for production of the protein; and optionally (b) recovering the protein.

12. The process of claim 1, wherein the polypeptide having beta-xylosidase activity comprises SEQ ID NO: 2 or amino acids 19 to 570 of SEQ ID NO: 2.

13. The process of claim 1, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

14. The process of claim 2, wherein the polypeptide having beta-xylosidase activity comprises SEQ ID NO: 2 or amino acids 19 to 570 of SEQ ID NO: 2.

15. The process of claim 2, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

16. The process of claim 2, wherein steps (a) and (b) are performed simultaneously in a simultaneous saccharification and fermentation.

17. The process of claim 3, wherein the polypeptide having beta-xylosidase activity comprises SEQ ID NO: 2 or amino acids 19 to 570 of SEQ ID NO: 2.

18. The process of claim 3, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

19. The process of claim 3, wherein the fermenting of the cellulosic or xylan-containing material produces a fermentation product.

20. The nucleic acid construct of claim 4, wherein the polypeptide having beta-xylosidase activity comprises SEQ ID NO: 2 or amino acids 19 to 570 of SEQ ID NO: 2.

* * * * *